(12) United States Patent
Kellar et al.

(10) Patent No.: US 7,235,052 B2
(45) Date of Patent: Jun. 26, 2007

(54) ULTRASOUND DETECTABLE INSTRUMENT WITH BUBBLE GENERATOR

(75) Inventors: Ewen James Crawford Kellar, Great Abington (GB); Seyed Mehdi Tavakoli, Great Abington (GB)

(73) Assignee: BTG International Limited, London (GB)

( * ) Notice: Subject to any disclaimer, the term of this patent is extended or adjusted under 35 U.S.C. 154(b) by 352 days.

(21) Appl. No.: 10/690,828

(22) Filed: Oct. 23, 2003

(65) Prior Publication Data

US 2004/0138566 A1    Jul. 15, 2004

Related U.S. Application Data

(63) Continuation of application No. 09/984,147, filed on Oct. 29, 2001, now abandoned, which is a continuation of application No. PCT/GB00/01451, filed on Apr. 17, 2000.

(30) Foreign Application Priority Data

Apr. 28, 1999    (GB)    ................ 9909801.4

(51) Int. Cl.
    *A61B 8/12*    (2006.01)
(52) U.S. Cl. ...................... 600/458; 600/462

(58) Field of Classification Search ................ 600/437, 600/458, 443, 462–471; 424/9.5–9.53
See application file for complete search history.

(56) References Cited

U.S. PATENT DOCUMENTS

| | | | |
|---|---|---|---|
| 5,415,870 A | 5/1995 | Gergely et al. | 424/464 |
| 5,786,069 A | 7/1998 | Ljungberg et al. | 428/216 |
| 5,824,339 A | 10/1998 | Shimizu et al. | 424/465 |
| 5,885,281 A | 3/1999 | Urueta | 606/45 |
| 5,912,012 A | 6/1999 | Carlin et al. | 424/464 |
| 6,106,473 A | 8/2000 | Violante et al. | 427/2.11 |
| 6,306,094 B1 | 10/2001 | Joseph | 600/458 |
| 6,749,554 B1 * | 6/2004 | Snow et al. | 600/3 |

FOREIGN PATENT DOCUMENTS

| | | |
|---|---|---|
| EP | 0 624 342 A1 | 11/1994 |
| WO | 98/18387 | 5/1998 |
| WO | 98/19713 | 5/1998 |

* cited by examiner

*Primary Examiner*—Francis J. Jaworski
(74) *Attorney, Agent, or Firm*—Nixon & Vanderhye

(57) ABSTRACT

Ultrasound detectable instrument including a bubble generator having two elements which, upon contact with each other in the presence of a fluid, react with each other to produce gas bubbles which may be detected by sonic imaging equipment. The two elements comprise first and second radially displaced layers of the elements within a fluid permeable carrier material.

32 Claims, 21 Drawing Sheets

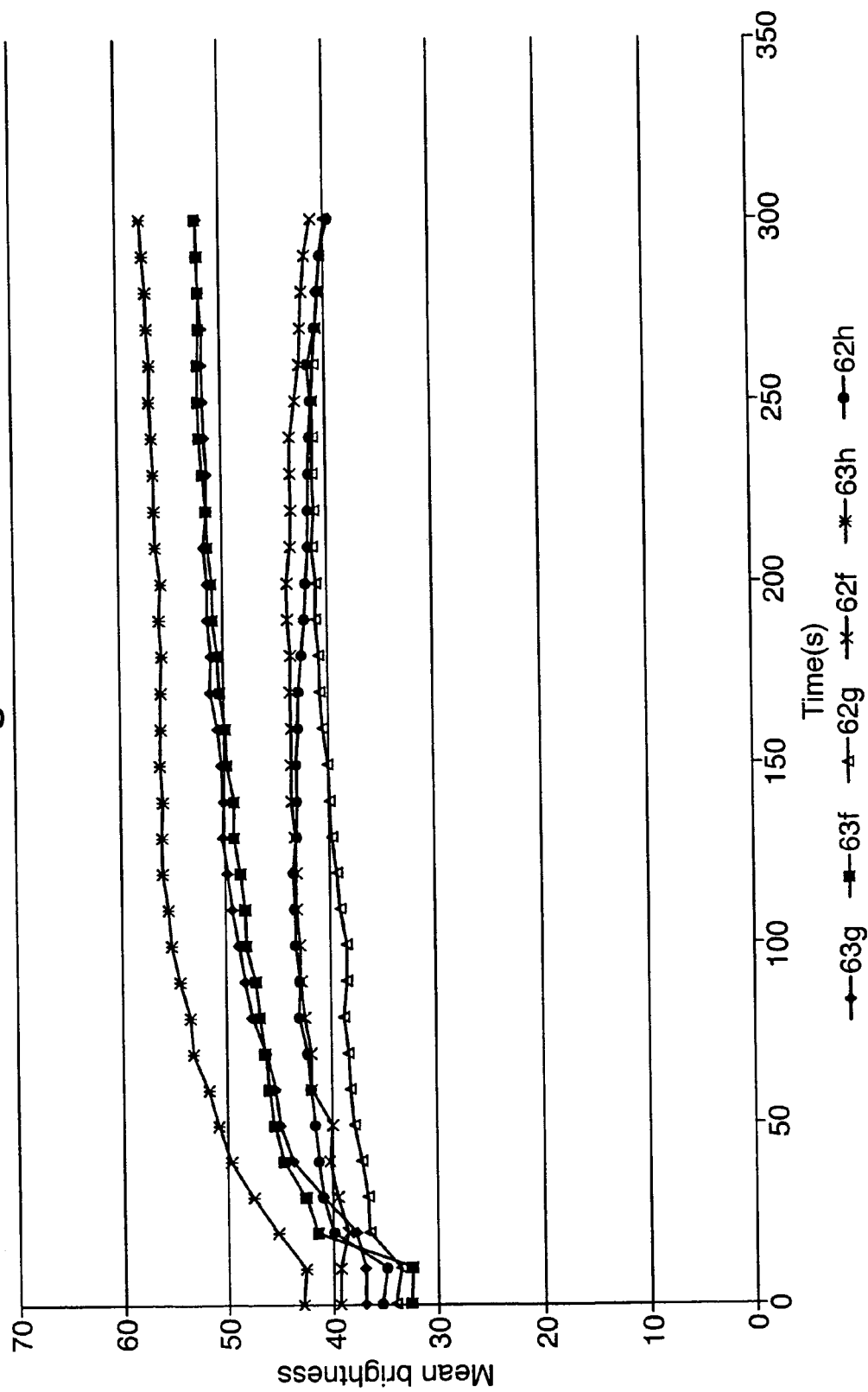

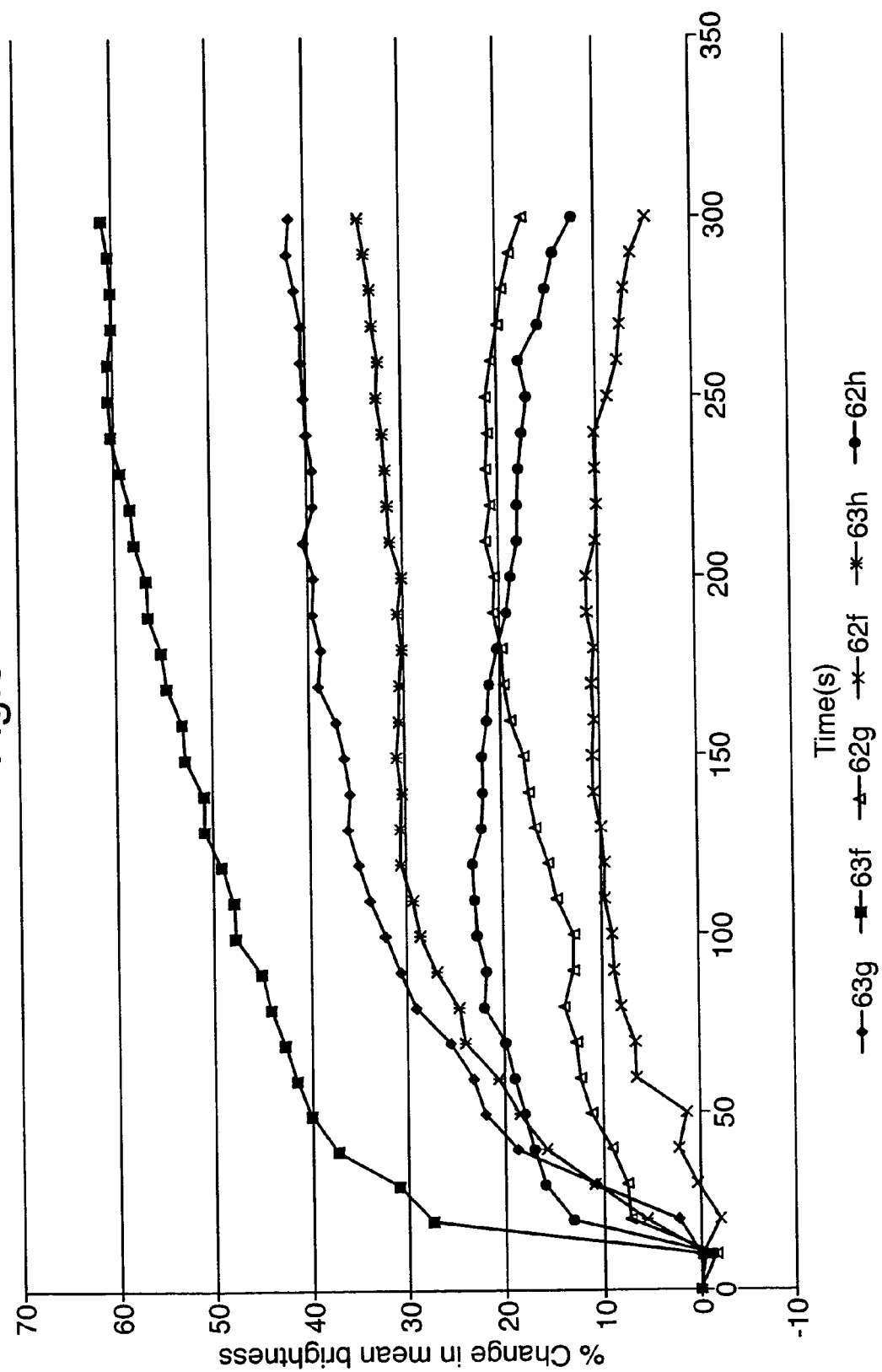

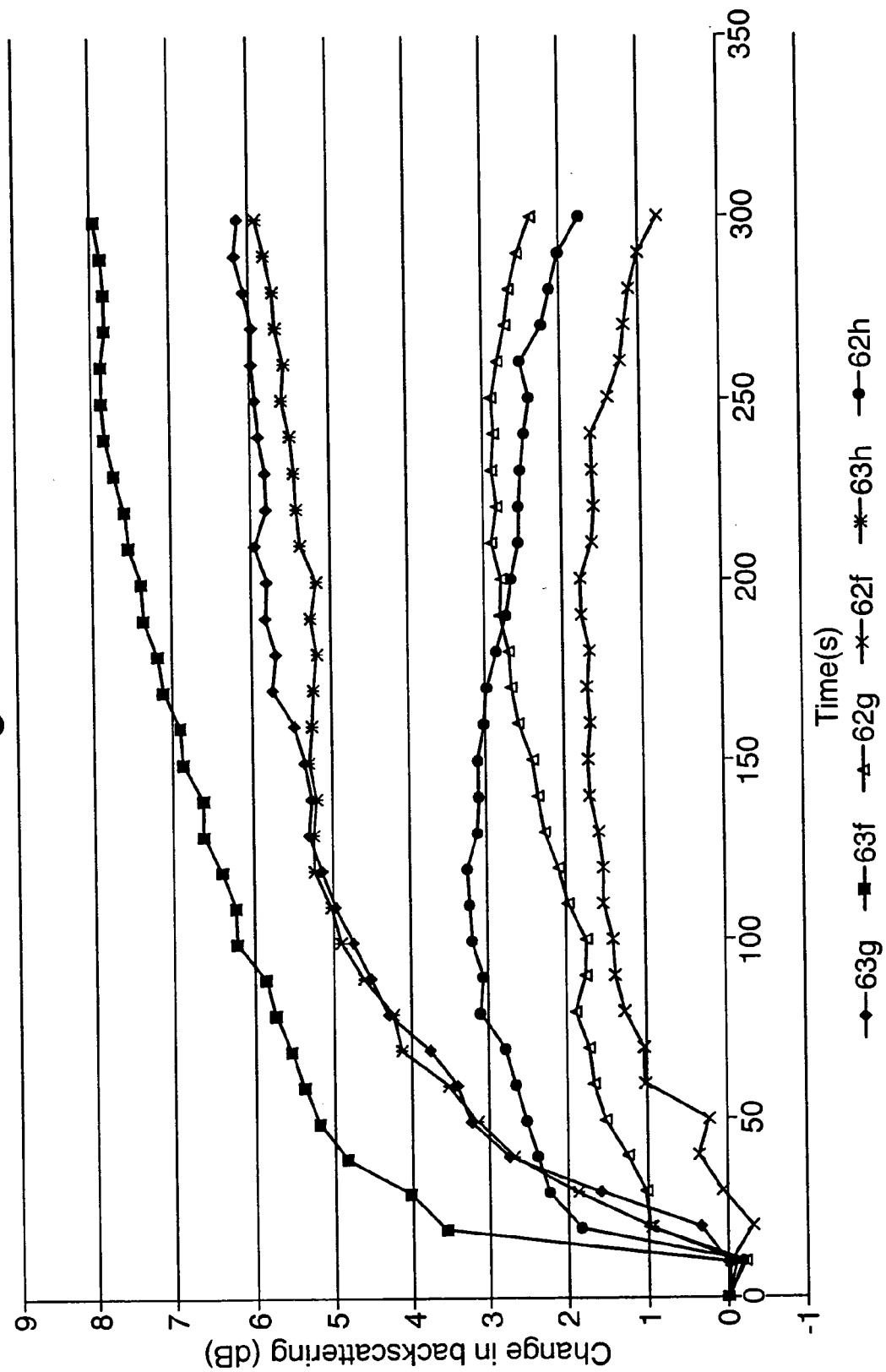

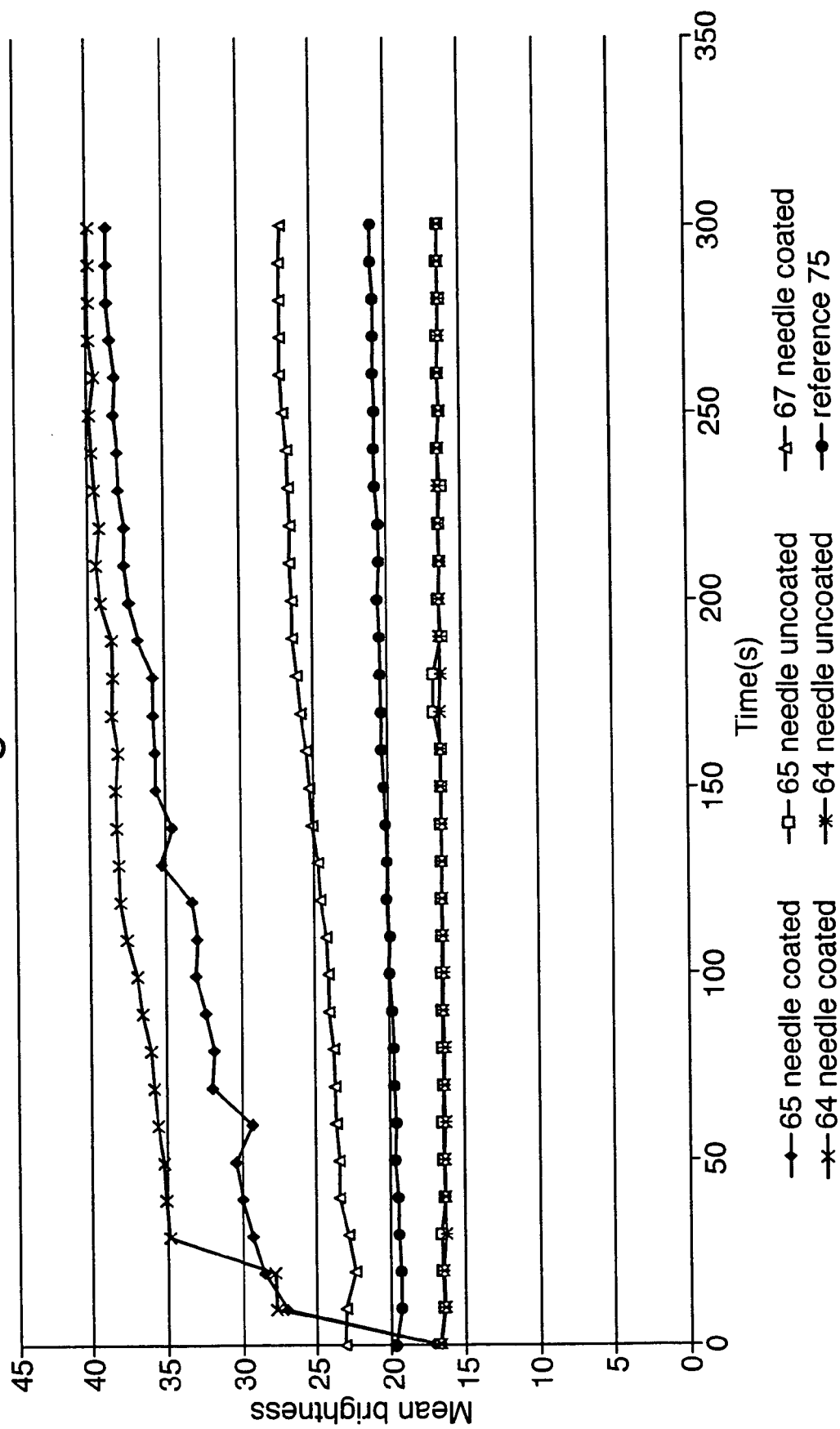

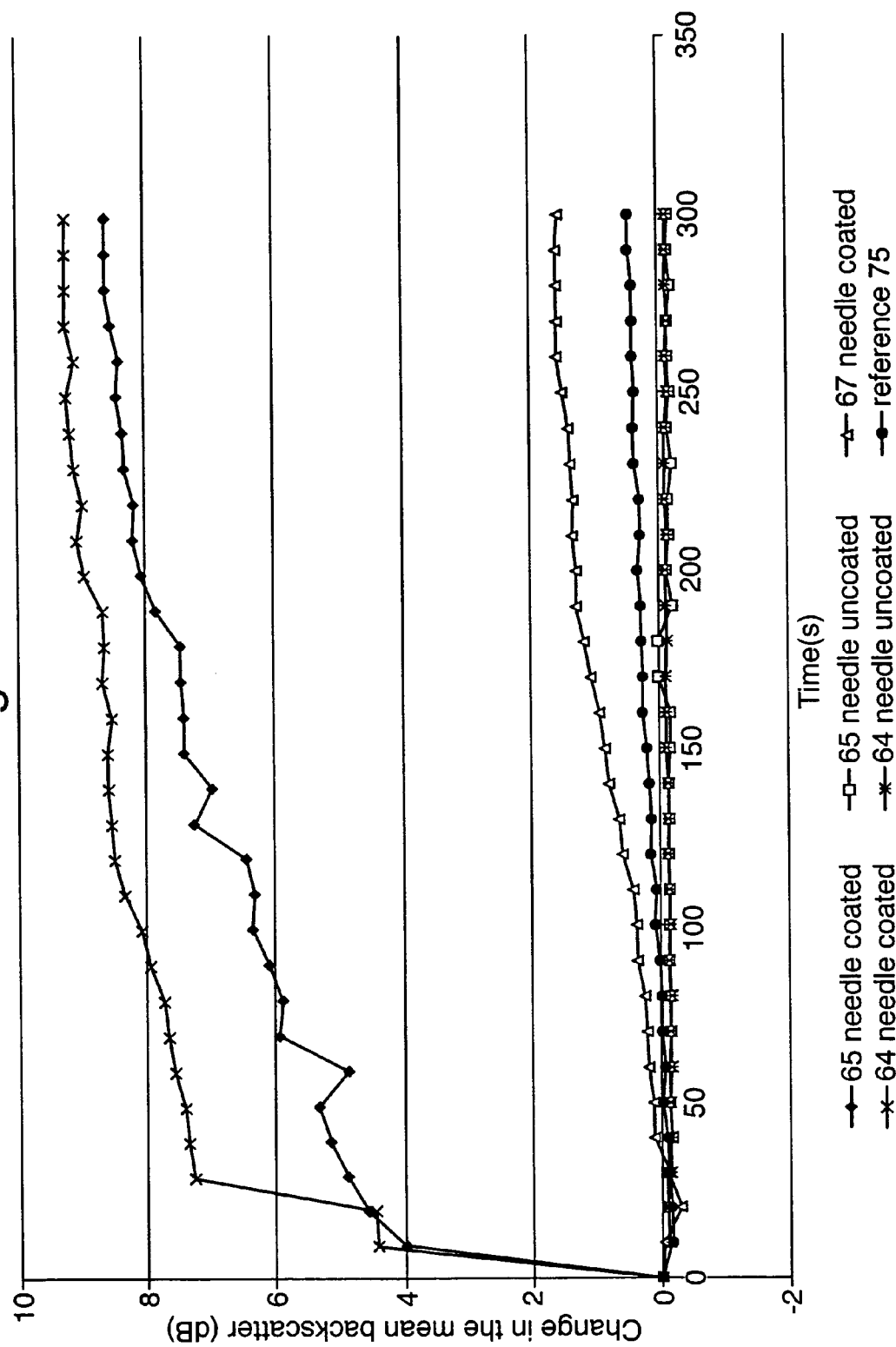

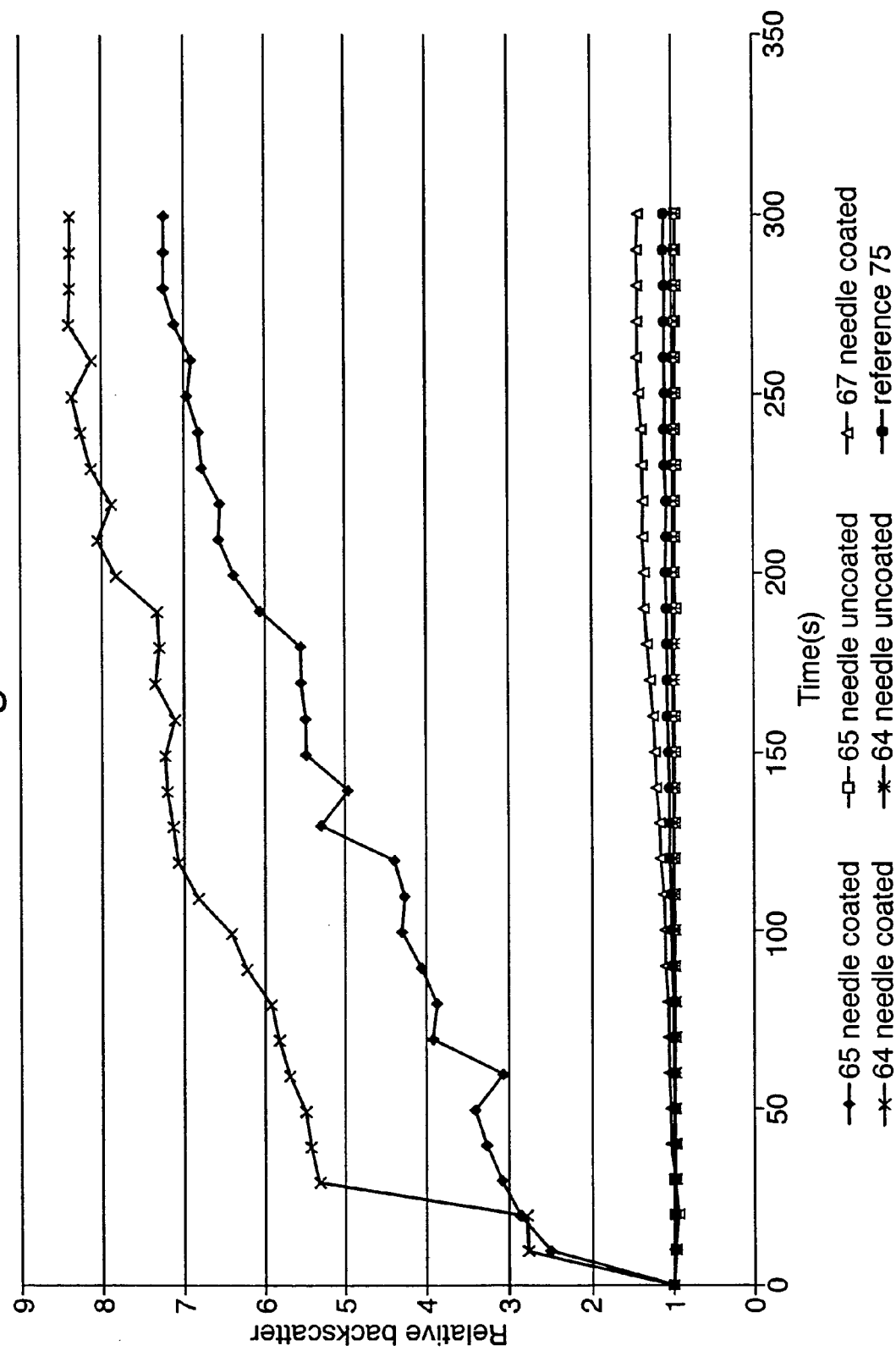

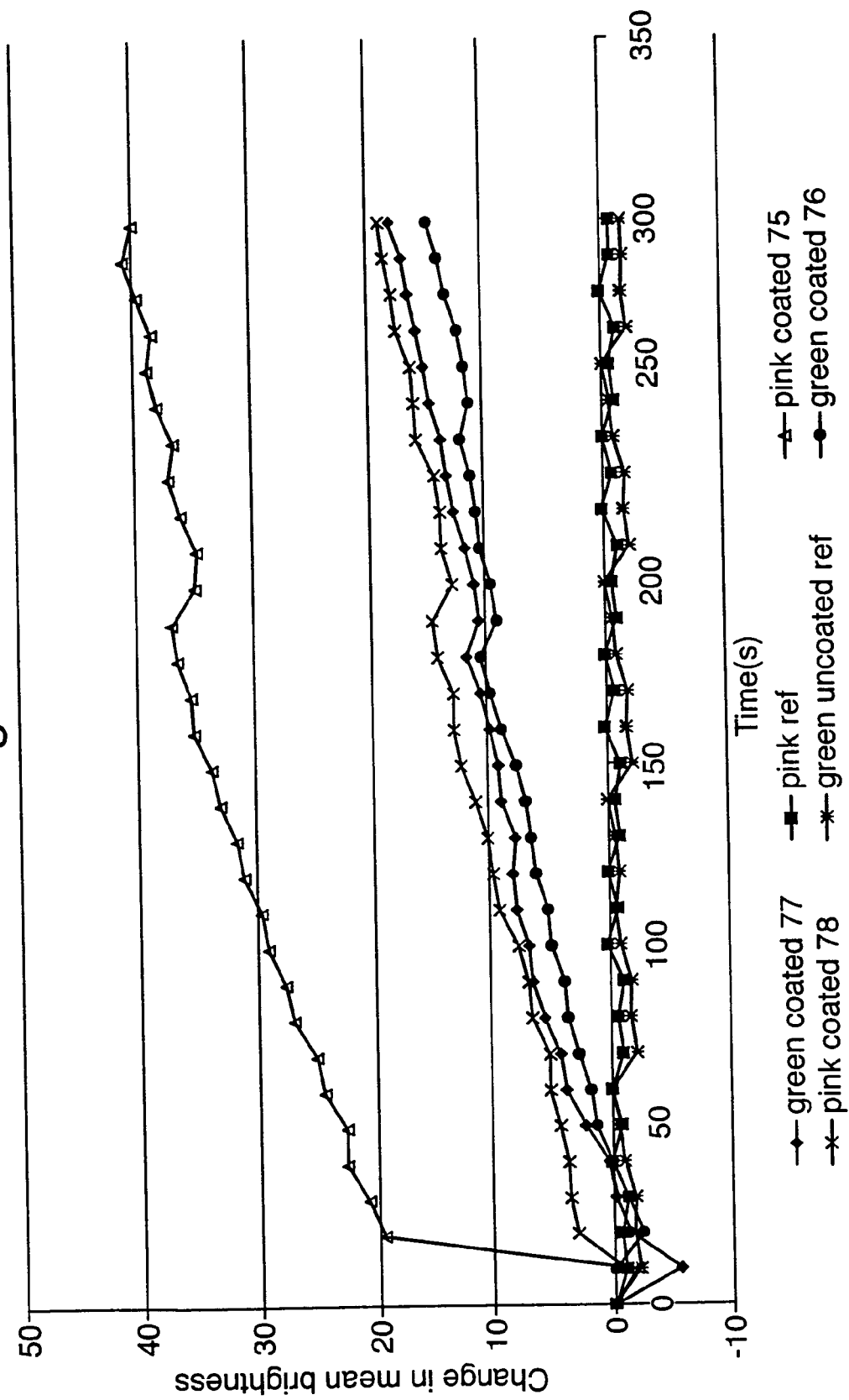

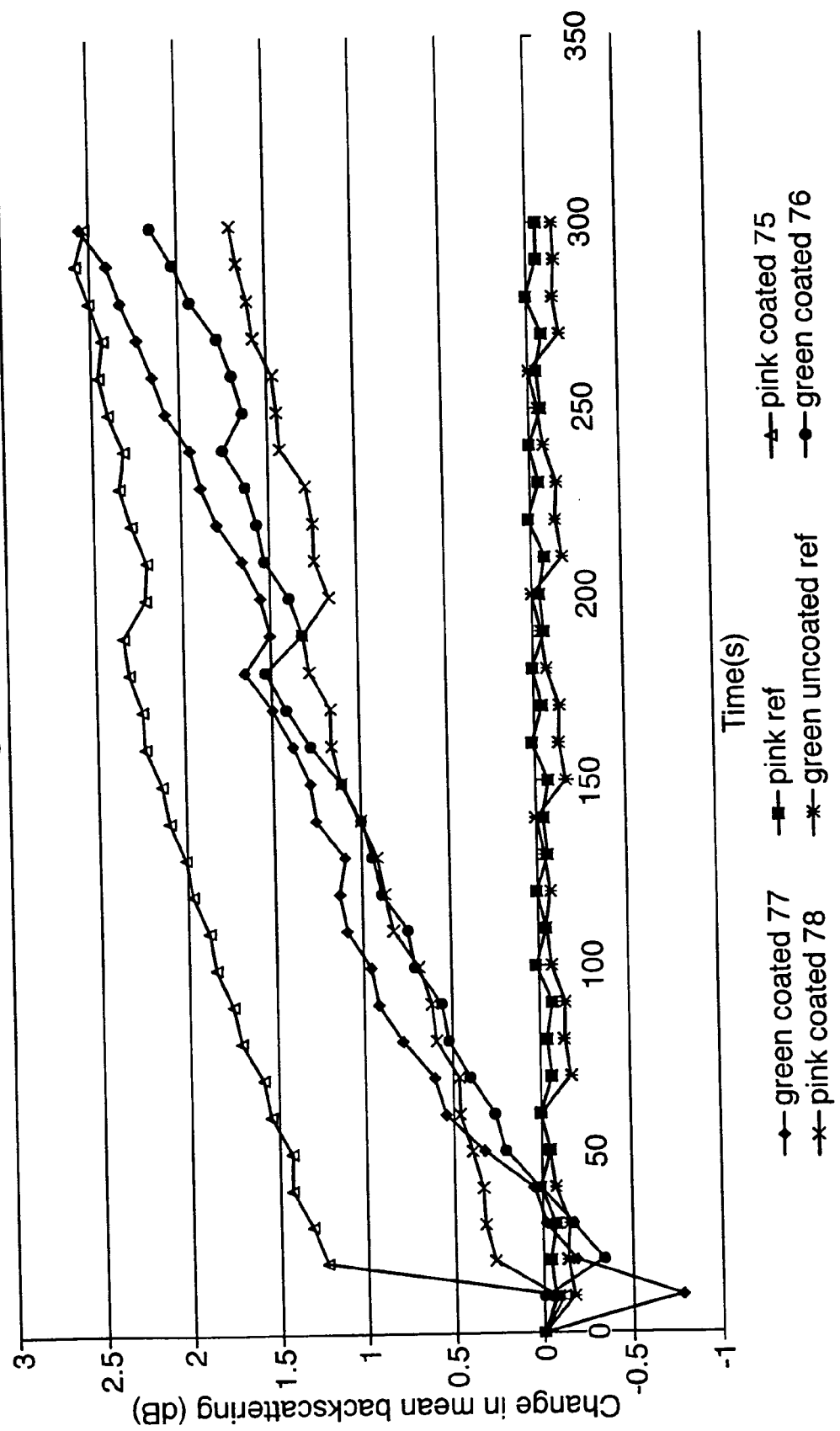

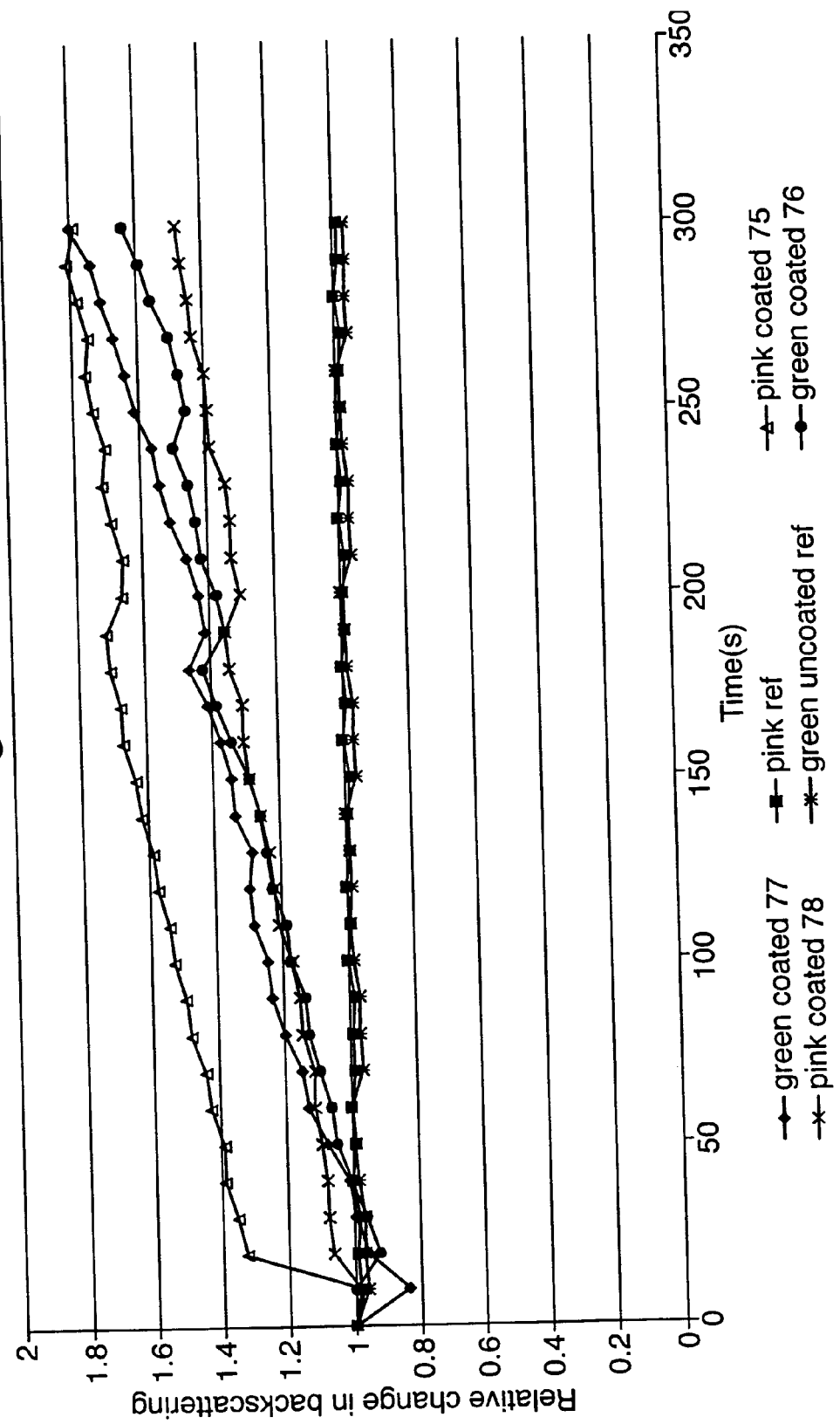

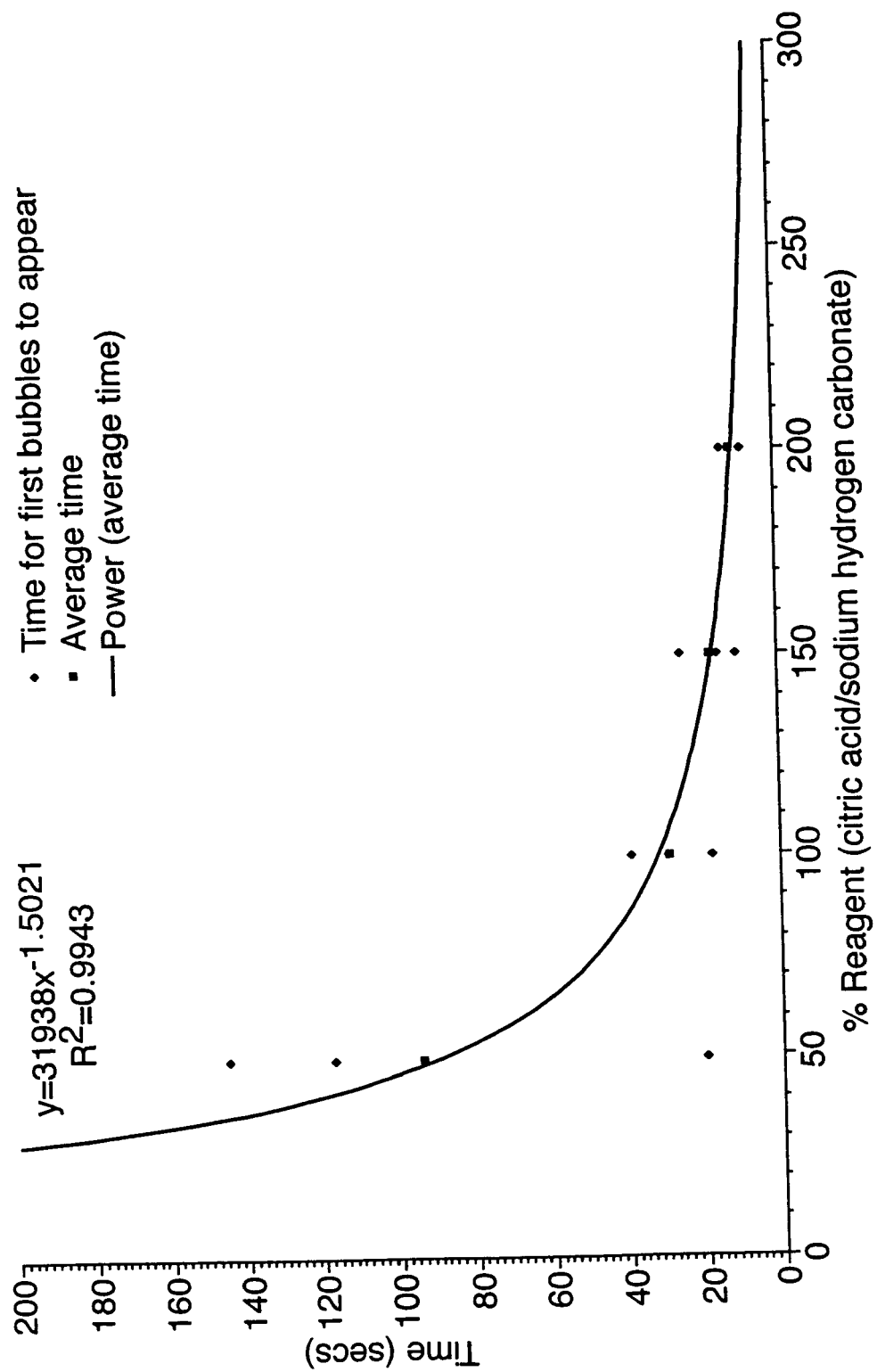

ULTRASOUND DETECTABLE INSTRUMENT WITH BUBBLE GENERATOR

This application is a continuation of application Ser. No. 09/984,147, filed Oct. 29, 2001 now abandoned, which is a continuation of application Ser. No. PCT/GB00/01451, filed Apr. 17, 2000, the entire content of which is hereby incorporated by reference in this application.

The present invention relates to an ultrasound reflective instrument and a method of manufacturing the same. The invention relates particularly, but not exclusively to such an instrument when suitable for use in medical applications.

BACKGROUND OF THE INVENTION

Presently known ultrasound visible instruments include that disclosed in WO 98/18387 which provides a probe insertable into a material containing a liquid and having a coating comprising a carrier material and a quantity of reactive material which, upon contacting a reactant, produces a quantity of bubbles adjacent the coating for reflecting ultrasonic energy. In the particular application, the probe comprises a biopsy needle and the coating is positioned towards a sharp distal end thereof, thereby to facilitate the guidance and positioning thereof. Alternatively the coating can be provided along the entire length of the instrument or at discrete portions along its length. The reactive material comprises, for example, a mixture of sodium hydrogen carbonate and citric powder contained within a single layer of a carrier material which facilitates interaction between an externally supplied fluid and the reactant. In operation, the fluid permeates through the carrier material and, once the two reactive components are wetted thereby a reaction takes places which produces a plurality of bubbles which are mobile within the carrier material in a manner which enhances the ultrasound reflectivity of such of a device over and above that presently known from similar devices.

SUMMARY OF THE INVENTION

It is an object of the present invention to improve still further the ultrasound reflectivity of such instruments, thereby to enhance the performance and use thereof. Additionally, the present invention aims to provide a method of manufacturing such an instrument.

Accordingly, the present invention provides an instrument insertable into a medium and being capable of detection by sonic imaging equipment comprising:

an elongate member, for insertion into said medium and having a region the position of which it is desirable to monitor;

bubble generating means for generating a plurality of discrete mobile bubbles at said region, whereby said bubbles are detectable by sonic imaging equipment, characterised in that:

said bubble generating means comprises two elements which, upon contacting with each other in the presence of a fluid, react with each other to produce said gas bubbles and in which said elements comprise first and second radially displaced layers of said elements within a fluid permeable carrier material.

Preferably, the instrument further includes a fluid permeable intermediate layer between said two element containing layers Advantageously, the instrument further includes a foundation layer on said instrument upon which are deposited said element containing layers.

Conveniently, said foundation layer comprises a fluid permeable layer.

Preferably, the instrument includes a primer layer on said instrument upon which said fluid permeable carrier material is deposited.

Alternatively, the instrument includes a primer layer on said instrument upon which said fluid permeable foundation layer is situated.

The carrier material may comprise a hydrophilic material and preferably comprises Hydrothane™.

Preferably, the two elements comprise citric acid and sodium hydrogen carbonate.

In a particularly preferred form the citric acid comprises dissolved citric acid.

In one arrangement said first layer comprises a radially inner layer and comprises citric acid and said second layer comprises a radially outer layer and comprises sodium hydrogen carbonate.

In an alternative arrangement said first layer comprises a radially inner layer and comprises sodium hydrogen carbonate and said second layer comprises a radially outer layer and comprises citric acid.

The intermediate layer may comprise a hydrophilic material and preferably comprises Hydrothane™.

The elongate member may include a prepared surface prepared by solvent degreasing or wet blasting.

Advantageously said primer layer comprises an acid etched layer and preferably comprises a chromate free water based primer (Cytec BR6752) or Chronoflex™ AL80A.

Advantageously the ratio of bubble generating means to carry material in said first or said second layer is between 20% and 200% by weight.

Preferably, the ratio of the first to the second reactive agents is substantially 50/50 (by weight).

Advantageously, said bubble generating means is provided at one or more discrete portions along said elongate member.

In a high visibility arrangement said bubble generating means is provided along a substantial length of said elongate member.

According to another aspect of the present invention there is provided a method of producing an instrument comprising the steps of:

a) depositing onto the instrument a first layer containing a first of two elements which, upon contact with each other in the presence of a liquid, react with each other to produce gas bubbles, and b) depositing onto the first layer a second layer containing a second of said two elements.

The method may include the further step of depositing a fluid permeable intermediate layer between said first and second layers.

Advantageously, the method includes the further step of depositing a foundation layer on said instrument prior to deposition of said first layer.

Preferably, the foundation layer comprises a fluid permeable layer.

Advantageously, the method includes the further step of depositing a primer layer onto said instrument prior to any of the layers of claims 1 to 4.

Preferably, the first and second layers comprise a hydrophilic material.

Advantageously, said first and second layers comprise Hydrothane™.

Advantageously, said two elements comprise citric acid and sodium hydrogen carbonate.

Particularly advantageously, said two elements comprise dissolved citric acid and sodium carbonate particles.

In one arrangement said first layer comprises citric acid and said second layer comprises sodium hydrogen carbonate.

In an alternative arrangement said first layer comprises sodium hydrogen carbonate and said second layer comprises citric acid.

Advantageously, said intermediate layer comprises a hydrophilic material which preferably comprises Hydrothane™.

Preferably the method includes the further step of preparing the instrument surface by solvent degreasing or wet blasting.

Advantageously, said primer layer comprises an acid etched layer, preferably a chromate free water based primer (Cytec BR6752) or Chronoflex™ AL80A.

Preferably the method includes the step of adding the first and second elements to a carrier material to form said layers and in which said elements are added to said carrier material in a ratio of between 20% and 200% by weight.

Advantageously, the first and second reactive elements are added in a ratio of substantially 50/50 by weight.

In a preferred arrangement the method includes the step of applying the layers at one or more discrete portions along said elongate member.

In an alternative arrangement the method includes the step of applying the layers at one or more discrete portions along said elongate member.

BRIEF DESCRIPTION OF THE DRAWINGS

The present invention will now be more particularly described by way of example only with reference to the accompanying drawings in which:

FIGS. 9A–9D show a quantitative analysis of ultrasound data for "brightness" coating (63*f–h*) compared to a poor coating (62*f–h*) on a stainless steel plate;

FIGS. 10A–10D show a quantitative analysis of ultrasound data for "brightness" coating of a first trial stainless steel biopsy needle;

FIGS. 11A–11D show a further quantitative analysis of ultrasound data for "brightness" coating on a stainless steel boxing needle;

FIG. 13 is a plot showing the relationship between time for first bubbles to be observed and the concentration of reagent present within the coating.

DETAILED DESCRIPTION OF PREFERRED EMBODIMENTS

Figure 2:
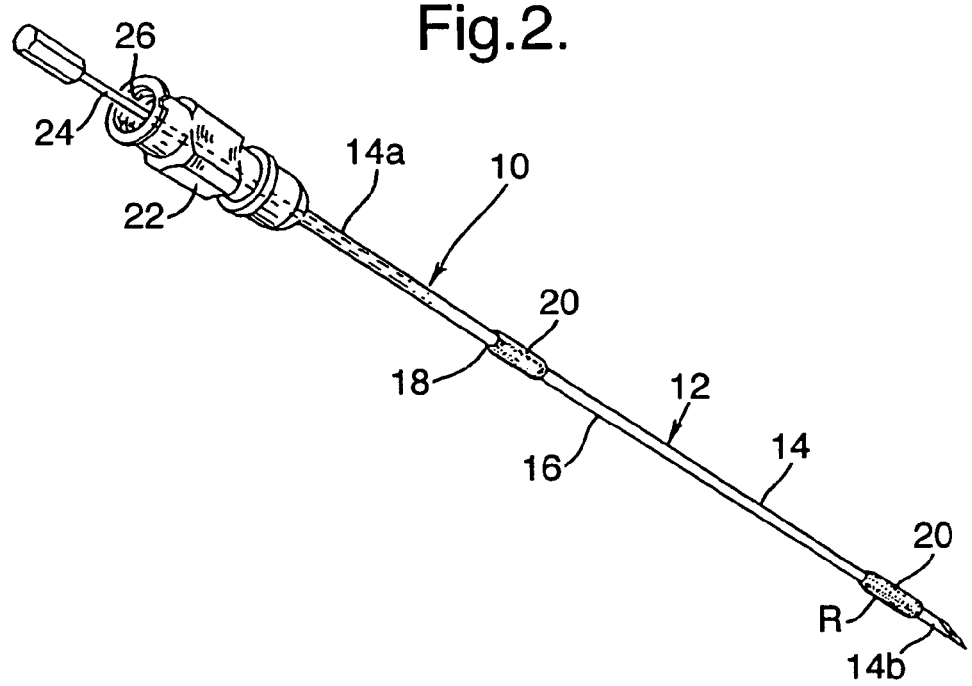
FIG. 2 is a perspective view of a biopsy needle in accordance with one aspect of the present invention.
Figure 3:
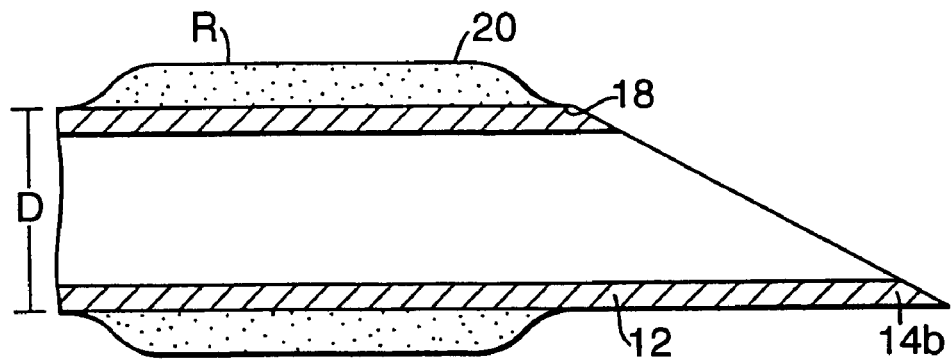
FIG. 3 is an enlarged cross-sectional view of a portion of the needle shown in FIG. 2.

Referring now to the drawings in generally but particularly to FIGS. 2 and 3, an instrument 10 in the form of, for example, biopsy needle 12 comprises an elongate needle 14 having proximal and distal ends 14*a*, 14*b*, the latter of which is sharply pointed. A cylindrical lumen 16 extends between the ends and provides a substantially smooth exterior surface 18 having one or more regions R upon which is deposited a coating 20, the function of which will be described in detail later herein. The needle 12 also includes a mounting 22 generally of a plastics material which surrounds and is secured to the proximal end. A stylet 24 is slidable and removably disposed within the lumen 16 and substantially blocks the distal end 14*b* and helps form a cutting edge for use during the insertion process. When removed the stylet 24 exposes a threaded or ribbed portion 26 on mounting 22 onto which a hypodermic syringe may be removably secured and used in a manner well known and therefore not described further herein.

The above-mentioned needle is employed in conjunction with a conventional ultrasound imaging apparatus well known to those skilled in the art and therefore not described in detail herein. The essential components of such a device are however shown in FIG. 1 and include an ultrasound transducer 52, signal processing means 54 for converting a received ultrasound signal into an electrical signal suitable for creating a display on a video monitor and a video monitor 56 for displaying said display.

Figure 8:
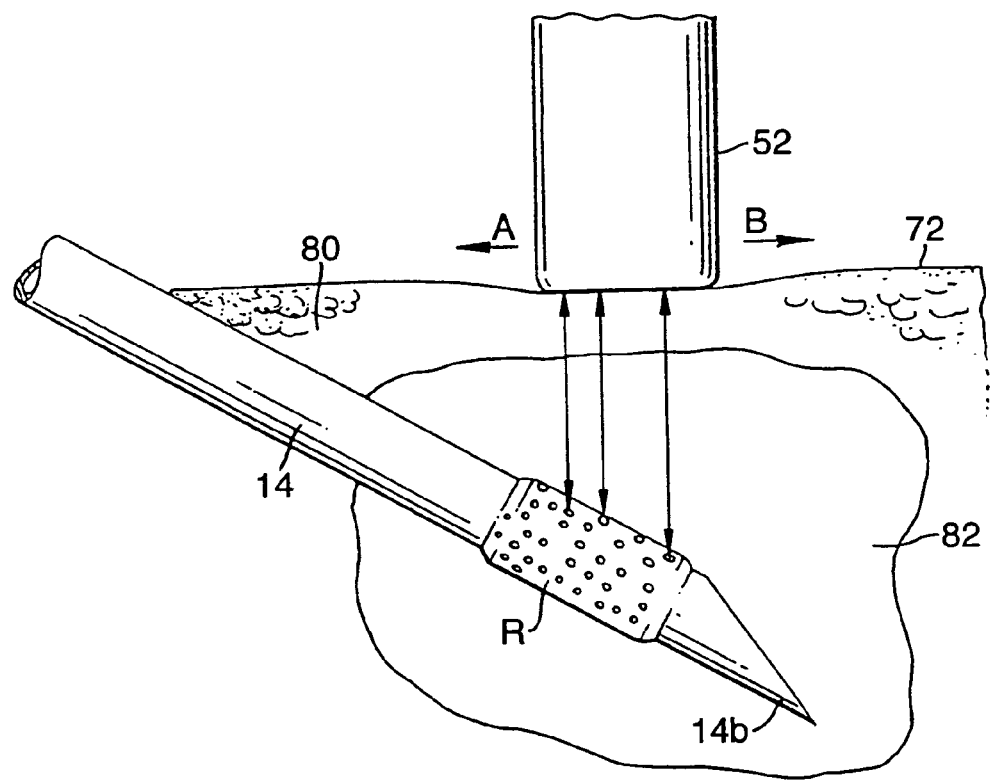
FIG. 8 is a schematic illustration of the present invention and an ultrasound transducer for emitting and receiving ultrasound energy.

Operation in the mode of the example is achieved by insertion of the needle 14 into, for example, human tissue 80 (FIG. 8) and then into the human organ under investigation, a portion of which is shown at 82 in FIG. 8. Once inserted, the effervescent material comes into contact with any fluid in said organ 82 and effervesces thereby to create a quantity of small gas bubbles as will be described below.

Figure 1:
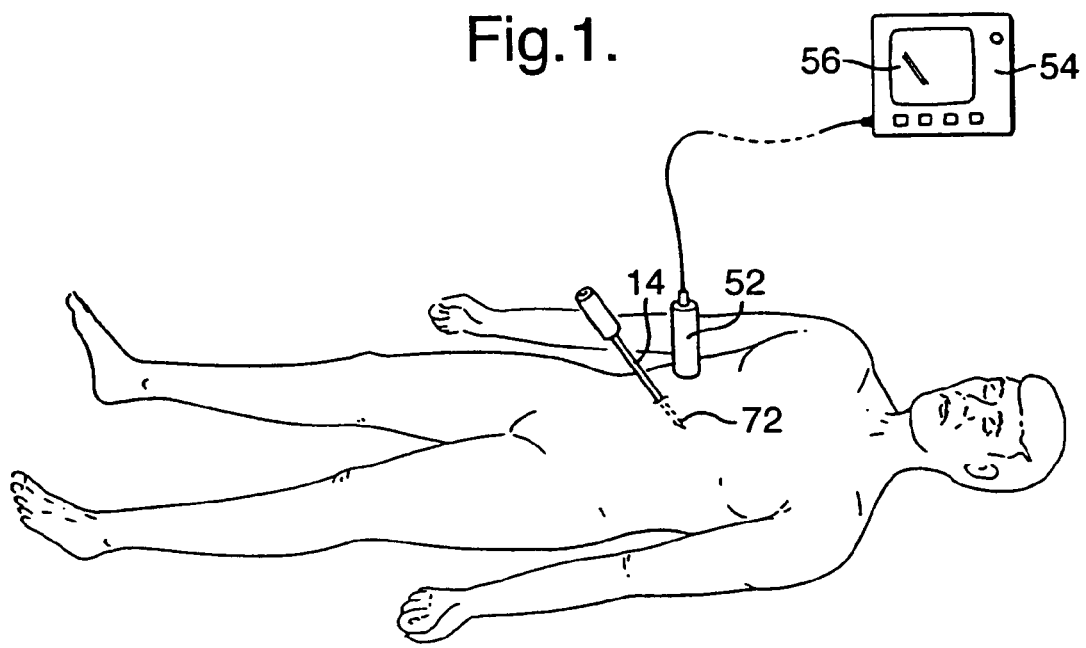
FIG. 1 is a general view of the present invention being used on a patient.

The ultrasound transducer 52 is placed on the outer surface 72 of, for example, the patient's body as shown in FIGS. 1 and 8 and acts to direct a quantity of ultrasonic energy in the general direction of the needle 14. The transducer 52 is then moved over surface 72 in the direction of arrows A, B until a reflection is detected from the highly reflective gas bubbles 64.

This text is taken from WO 98/18387 (pages 6 and 7) and was apparently omitted from the present application in error by the original draftsman.

Figure 4:
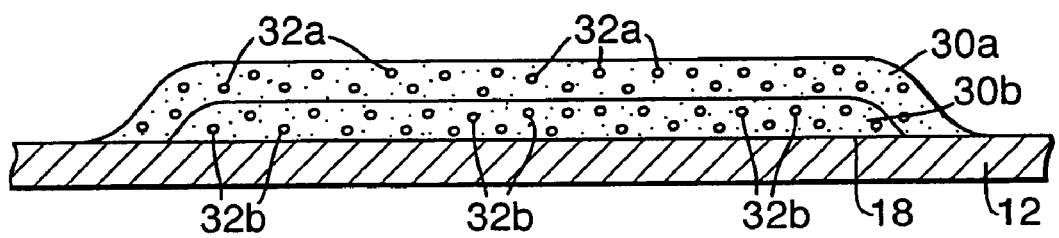
FIGS. 4–7 are enlarged cross-sectional views of various forms of the present invention.
Figure 5:
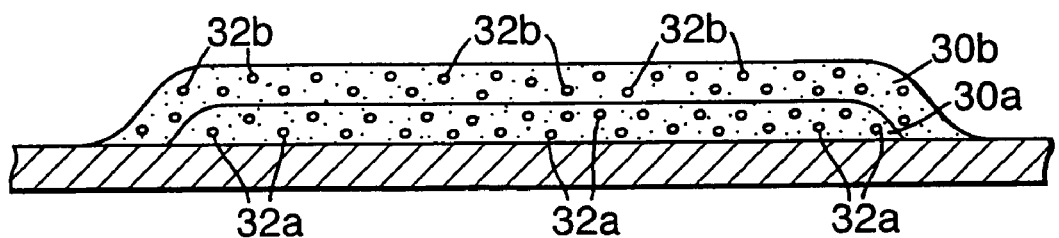
Figure 6:
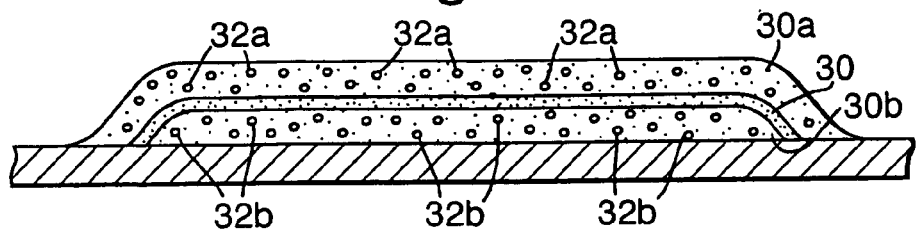

The instrument 10 of the present invention is characterised in that the coating 20 is of a multilayer construction as shown in detail in FIGS. 4–6. Whilst the detail of the coating will be discussed later herein, it is worth highlighting that the example of FIG. 3 shows the coating 20 positioned towards the distal end 14*b* of a needle which assists the accurate positioning of the end. Other positions may however be used to advantage and the distance between regions of deposited coating 20 may be preset thereby to assist in determining how deep the instrument has been inserted. Alternatively, when it is desirable to monitor the position of the entire needle, the coating may be provided along the entire length of the needle. The deposited coating 20 comprises a carrier material 30 and means for generating a plurality of very fine mobile gas bubbles. The function of the carrier material is to provide a matrix or support site for the bubble generating means which can take any one of a number of forms, examples of which are detailed below. In essence, the bubble generating means comprises a reactive substance which, upon interaction with a reactant acts to produce the required bubbles. A secondary function of the carrier material 30 is to provide a bulk of material which affords mobility of the bubbles to facilitate ultrasonic detection thereof. For enhanced performance, the carrier material may be chosen so as to have an ultrasonic impedance the same as or close to that of the material in which it is to be inserted. By matching the impedance in this manner, it is possible to reduce the reflections at the interface between the carrier material and the material in which it is inserted and increase the quantity of ultrasound interacting with the bubbles. Clearly, any such increase will enhance the quality of any reflected ultrasound signal.

In the arrangements of the present invention, the carrier material is used to radially separate the two elements 32a, 32b of the effervescent material (the reactive substance) such that, upon contact with a liquid (the reactant) the liquid must first permeate through the carrier material 30 and bubbling can only commence once a suitable saturation level has been achieved. The advantages of radial separation are discussed later herein. As in WO 98/18387 the bubbles are mobile in two senses. Firstly, they are mobile in the sense that they are able to migrate through the carrying material and, secondly, they are mobile in the sense that they grow in size as they develop. Typically, a bubble generated in this manner will grow into a bubble having a diameter of at least and generally greater than 5 microns. For optimum performance it has been found that a bubble size of between 30 and 50 microns and preferably approximately 40 microns is best. The carrier material 30 also acts to protect the effervescent material 32a, 32b which tends to be less robust and hence susceptible to damage during handling. In a preferred arrangement the carrier material comprises a hydrophilic material the advantages and function of which will be described later herein. Whilst it would be appreciated that any one of a number of materials could be employed to perform the function of the carrier material, it has been found that epoxy based resins are suitable for such applications. Such materials can be applied by a simple dipping technique followed by a curing step (which may simply comprise exposure to ambient air or may comprise a heating step) and are highly bio-compatible, should the instrument be required for use on a human or animal patient. A suitable material is polyurethane such as that sold under the trade name Hydrothane™ which can have a plurality of interconnecting pores or may be of a closed cellular structure and can be "engineered" to create a pore structure suitable for a particular application. Clearly, such materials lend themselves to use in the present invention in which it is desirable to produce an cellular structure through which generated bubbles are able to pass. Polyolefins such as polyethylene or polypropylene may also be suitable examples. Alternatively, one might use polystyrene which, whilst normally would be hydrophobic, can be manufactured in hydrophilic form. The effervescent material chosen may comprise a number of different elements but the examples shown herein comprise sodium hydrogen carbonate and citric acid powder. Such a material is highly bio-compatible and therefore presents little if any hazard when the needle is employed for use on the human or animal body. Other materials may be employed, particularly when bio-compatibility is not an issue. It is worth mentioning that the ratio of the two reactive substances to each other and the ratio of the total reactive substance to the carrier material each have a significant effect on the performance of the present invention.

Referring now more particularly to FIGS. 4–7, it will be appreciated that the two elements 32a, 32b may be radially separated in any one of a number of different ways. In the particular example of FIG. 4 the citric acid containing layer 30b is deposited first and a subsequent sodium hydrogen carbonate containing layer 30a is provided over the top thereof. Details of the deposition process are provided later herein. In this example, incoming fluid will transport at least a small portion of the sodium hydrogen carbonate through the cellular structure of the carrier material 30a and into the citric acid containing layer 30b such that the two elements may interact and produce the required bubble generating reaction. Once the two layers are completely wetted, reaction between the two elements is accelerated and bubbles are produced at a more rapid rate. Tests show that this arrangement can produce ultrasound detectable bubbles in as little as 8–20 seconds.

FIG. 5 illustrates the opposite arrangement in which the first deposited layer includes the sodium hydrogen layer carbonate 30a over which is deposited a second layer 30b containing the citric acid 32b. It has been found that this arrangement produces bubbles after some 6 minutes but these bubbles are still of a size suitable for use with ultrasound detecting apparatus. This arrangement might lend itself to situations where it is desirable to delay the generation of the bubbles.

FIG. 6 illustrates a modification of the arrangement shown in FIG. 4 in which an intermediate layer of carrier material 30 is provided in order to separate the two element containing layers 30a, 30b. The advantage of this arrangement resides in the fact that minimises reaction between layers as they are laid down.

Figure 7:
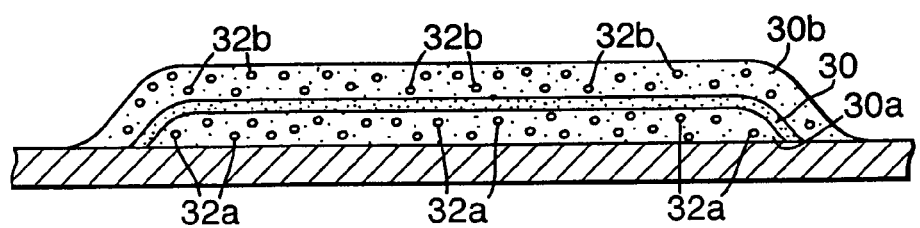

FIG. 7 illustrates the reverse arrangement of FIG. 6 in which the sodium hydrogen carbonate containing layer 30a is deposited first and separated from the citric acid containing layer 30b by an intermediate barrier layer 30 comprising carrier material. Again, separation of the two elements 32a, 32b from each other by an intermediate layer helps regulate the rate at which bubbles are generated.

Details of work carried out in association with the present invention will now be described with reference to the three main areas of:

adhesion enhancement of the coating to a stainless steel substrate;

concentration of the gas producing agents; and the distribution of the gas producing agents within the carrier material. Each of these areas is now discussed in detail and the conclusions of the tests are outlined below.

1.1. Materials

Materials used in coating formulation were as follows:
(i) Polymer: Polyurethane support matrix, Hydrothane™ (Cardio Tech International Ltd).
(ii) Gas Producing agent:
Sodium hydrogen carbonate (99.74% A.C.S. Reagent from Aldrich Chemical Co.) (Cat No. 23,652-7).
Citric acid (99% powder form from Aldrich Chemical Co.) (Cat. No. C8,315-5)
(iii) Solvent: Tetrahydrofuran (THF), HPLC grade unstabilised from Fisher Scientific for dissolving polyurethanes.

Material used for surface pre-treatment of stainless steel were as follows:
(i) Degreasing solvent: Acetone (Aldrich Chemical Co).
(ii) Wet blasting medium: Alumina grit (60 mesh) from Vapormatt/Hydrate Systems Ltd.
(iii) Etch solution:
a) HCl (Aldrich Chemical Co).
b) $FeCl_2$ (Aldrich Chemical Co).

(iv) Primers:
  a) Cytec BR6757 (Cytec Fiberite) water based primer system.
  b) Chronoflex™ (Cardio Tech International Ltd) a polyurethane based primer.

The substrate upon which the coating were applied were:
(i) Glass slides (provided by TWI).
(ii) Stainless steel plates (provided by TWI).
(iii) Biopsy needles of two different gauges were used for this series of experiments. For convenience, the needles are hereafter referred to by the colours of the respective needle hubs. Each needle consisted of a solid inner stylus and hollow outer cannula, the dimensions of which are given below.

| Needle Diameter | Stylus Diameter | Cannular Diameter |
|---|---|---|
| Green (G21) | 0.44 mm | 0.94 mm |
| Pink (G18) | 0.76 mm | 1.17 mm |

The needles were provided by St George's Hospital.
Ultrasound experiments were carried out using:
Tissue-Mimicking Material (TMM)—prepared at St George's Hospital.
Acoustic properties of TMM:

| | |
|---|---|
| Speed of sound propagation | 1551 m · s$^{-1}$ |
| Density | 1050 Kg · m$^{-3}$ |
| Attenuation coefficient | 0.5 dB · cm$^{-1}$ |
| Back cross-section per unit volume | $2.2 \times 10^{-3}$ · cm$^{-1}$ · Sr$^{-1}$ |

Isolated ovine liver—prepared at St George's Hospital.

1.2. Surface Treatment of Stainless Steel

Adhesion evaluation of the coating to stainless steel was carried out with five different surface pretreatments for stainless steel. These were:
(i) Degreased only (acetone). Samples were degreased using an acetone soaked lint free cloth and the solvent allowed to evaporate before coating.
(ii) Degreased in acetone and wet blasted (Vapormate T0899 wet blasting booth, Vapormatt Ltd) for 60–90 seconds using 60 mesh alumina grit with water as a propellant. The blast pressure was 4 bar (2956 mmHg). Samples were then allowed to dry in air before a second degreasing and coating.
(iii) Degreased in acetone, wet blasted, degreased in acetone again and then primed with Chronoflexm AL80A. A solution of 6.5%/wt (0.0575 g/ml) Chronoflex™ AL80A was produced using the same pre-soak and reflux method used to dissolve Hydrothane™ as described in Report 1, section 3.2.1.5. The primer was painted on and allowed to dry prior to coating.
(iv) Degreased in acetone, wet blasted, degreased in acetone again and etched using HCl/FeCl$_2$ at 20° C. The etch solution comprised of a 50/50 mixture by wt of FeCl$_2$ and HCl (concentration 35–37% in water). Etching was achieved by immersing the sample surfaces to be bonded in the etch for 10 minutes at room temperature. Samples were washed in tap water and air dried prior to coating.
(v) Degreased in acetone, wet blasted, degreased in acetone again and then primed using Cytec 6757 water based primer. The primer was applied to the surface by spraying, allowing it to dry and then the samples were baked in a fan assisted oven at 120° C. for one hour.

2. Assessment Techniques

The following assessment techniques were used to evaluate the coating and its performance.

2.1. Adhesion Tests

These tests were based upon the 180° peel test, ISO 8510-2.

Evaluation was conducted according to a modified version of the 180° peel test (ISO 8510-2, ) where a strip of polycotton was used as a flexible support for the coating material. A layer of Hydrothane™ was applied to the surface of the plate and before all the solvent had evaporated, a second layer was applied, immediately followed by a strip of polycotton. The top surface of the polycotton was then completely wetted with subsequent applications of the Hydrothane™ solution to ensure adequate adhesion of the polycotton to the base layer of polyurethane.

Limitations to the length of plate available (100 mm) required the test be modified, despite the test standard stipulating a minimum length of 200 mm. This was deemed acceptable, in view of the fact that the experiment was qualitative in nature, enabling a comparison to be made between the five pretreatments. A total of five peel tests was carried out for each surface pretreatment condition, for both dry and wet samples. In the case of the wet samples the test was conducted on each sample after it had been immersed in water for three minutes.

2.2. Video Imaging

To assess the real-time performance of the coating materials, a Microvision MV2100 CCD camera with a MV—120z microscope attachment was used in conjunction with a video recorder, Sony U-Matic V0-8800P. By placing the coated materials (stainless steel plate or biopsy needle) in a glass dish filled with water, the bubble production activity of the coatings could be monitored.

Selected recorded video data was then transferred as MPEG files onto a CD-ROM disk, which enabled the following factors to be assessed:
Time to produced first bubbles.
Duration of bubbling.
Size of bubbles.
Location/distribution of bubbles.
Other effects of water on the coating e.g. disbanding etc.

2.3. MICROSCOPY

Optical analysis was carried out using two instruments:
An Olympus BH2 microscope using polarised light. Photographs were taken with an Olympus PM-10AD camera system.
A Leica WILDM3Z binocular microscope with an Olympus PM-10AD camera system.

2.4. Ultrasound

The samples were analysed at St. George's Hospital using an HDI 1000 "Apogee" ultrasound system (Advanced Technology Laboratories), set at the lowest gain, and fitted with a 3.5 MHz annular sector probe. The probe was fixed just under the surface of the water in a thermostatically-controlled water bath, maintained at 37° C. The angle of inclination of the probe and the depth to which it was immersed were kept constant throughout the experiments.

The test samples were placed in a fixed position relative to the probe and supported on a steel block immersed in the water bath. This ensured that scatter from the generated bubbles and the coated surface, rather than specular reflection, was responsible for the returning echoes. The distance from the probe, together with the horizontal orientation of the samples, gave the least sensitive position for recording the echo intensities. In vivo, the angle of the coated needle would be more conducive to reflection and should give higher intensity echoes.

N.B. Where reference is made to f, g or h for a particular needle, this reference is to a first, second and third example of the needle having the composition associated with the reference number associated therewith. Any reference to "needle uncoated" indicates that the needle in question is one which has had a coating removed after testing in order to provide a reference datum.

3. Results and Discussion

3.1. Reassessment of Previous Data, Using Software Analysis

Software was developed by the Medical Physics Department at St. George's Hospital to enable quantitative analysis to be carried out on the ultrasound image data acquired during earlier trials. This analysis, performed as a precursor to the work carried out had two objectives:
1. To develop an algorithm which would enable ultrasound image data acquired from both previous and current work to be assessed in a rapid, semi-automatic way.
2. To analyse the previous data using the above algorithm, in order to corroborate the visual conclusions drawn from the earlier results.

3.1.1. Methodology for Analysis

The mean brightness of a region of interest of each of the digitised images (512×512×8 bit format) was calculated and expressed as follows:
1. Mean brightness vs time.
2. Percentage change in mean brightness vs time.
3. Change in mean brightness in dB against background vs time.
4. Relative backscatter with respect to background vs time.

The coated samples which demonstrated the greatest change in brightness were selected for further optimisation of materials and coating methods. The following table details the composition of those samples which were of interest.

| No. | Coating Structure | Composition | Colour |
|---|---|---|---|
| 62 | St/PUC/PU/PUS | [PUC 50%, PUS 40%] | |
| 63 | St/PU/PUC/PU/PUS/PU | [PUC 50%, PUS 40%] | |
| 64 | St/PUC/PU/PUS | [PUC 50%, PUS 40%] | Pink |
| 65 | St/PUC/PU/PUS | [PUC 50%, PUS 40%] | Green |
| 67 | St/PU/PUC/PU/PUS/PU | [PUC 50%, PUS 40%] | Green |
| 75 | St/PU/PUC/PU/PUS | [PUC 60%, PUS 50%] | Pink |
| 76 | St/PU/PUC/PU/PUS | [PUC 60%, PUS 50%] | Green |
| 77 | St/PU/PUC/PU/PUS | [PUC 80%, PUS 70%] | Green |
| 78 | St/PU/PUC/PU/PUS | [PUC 80%, PUS 70%] | Pink |

3.1.2. Results from Retrospective Analysis

Figure 9D:
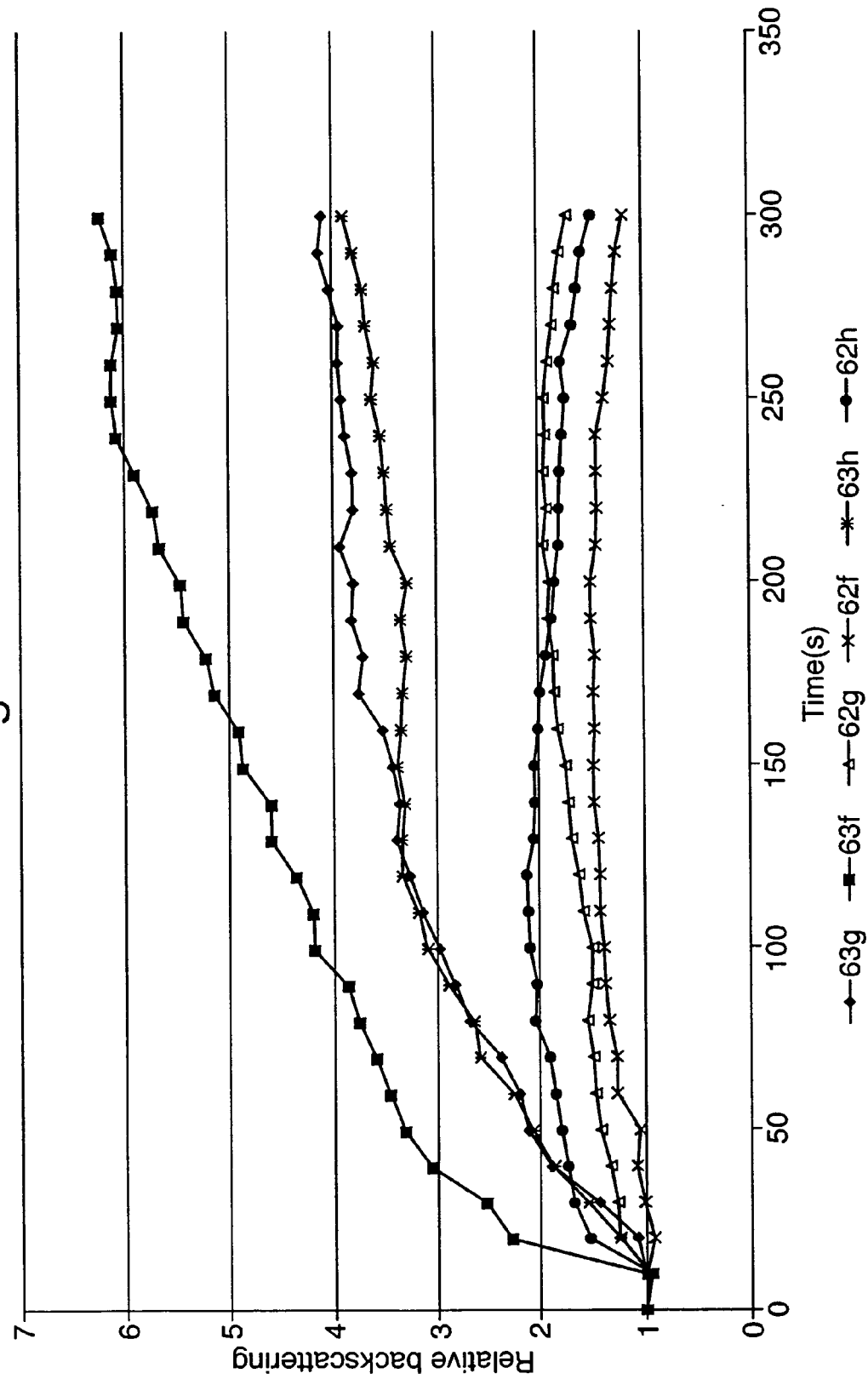
Figure 10B:
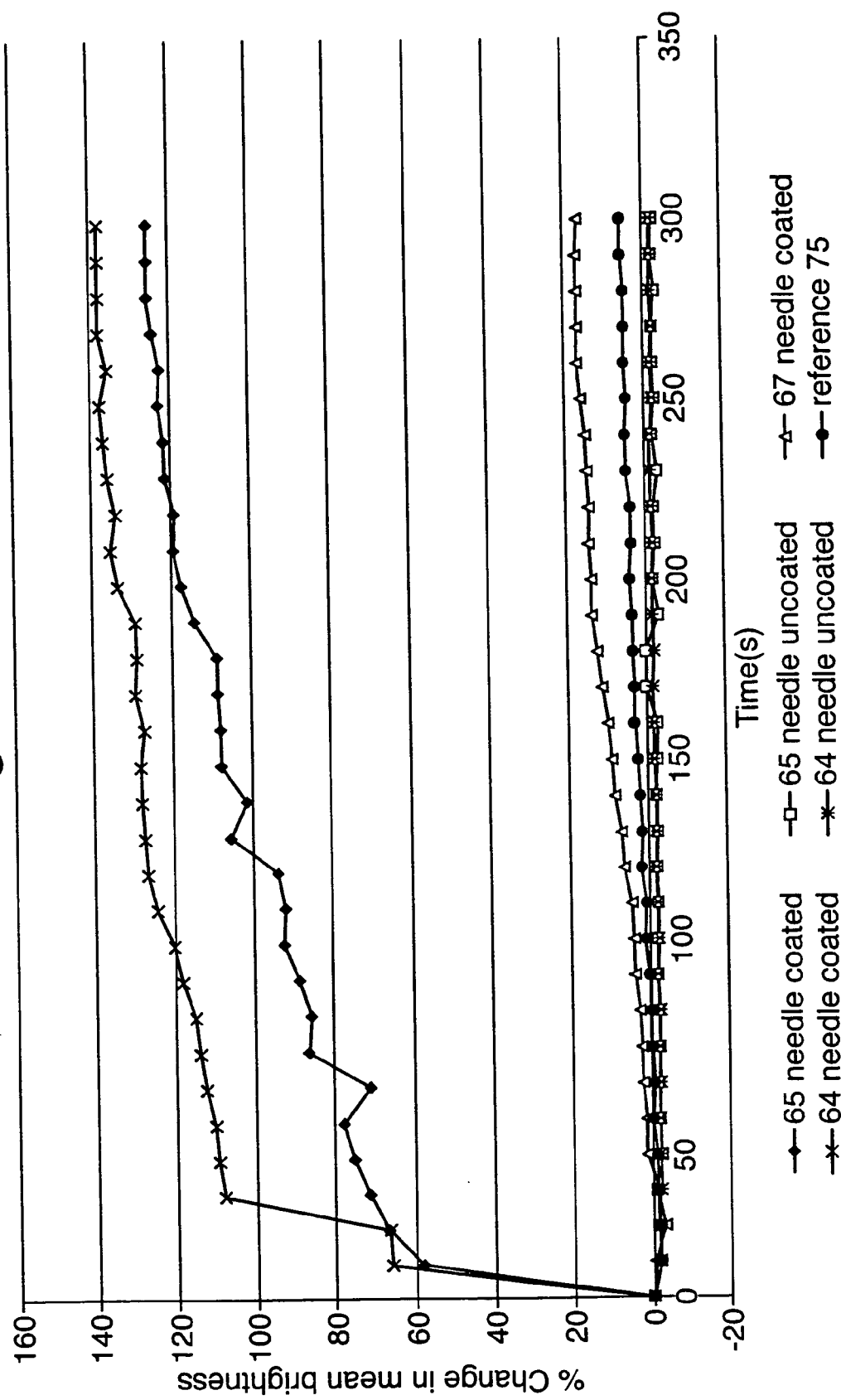
Figure 11A:
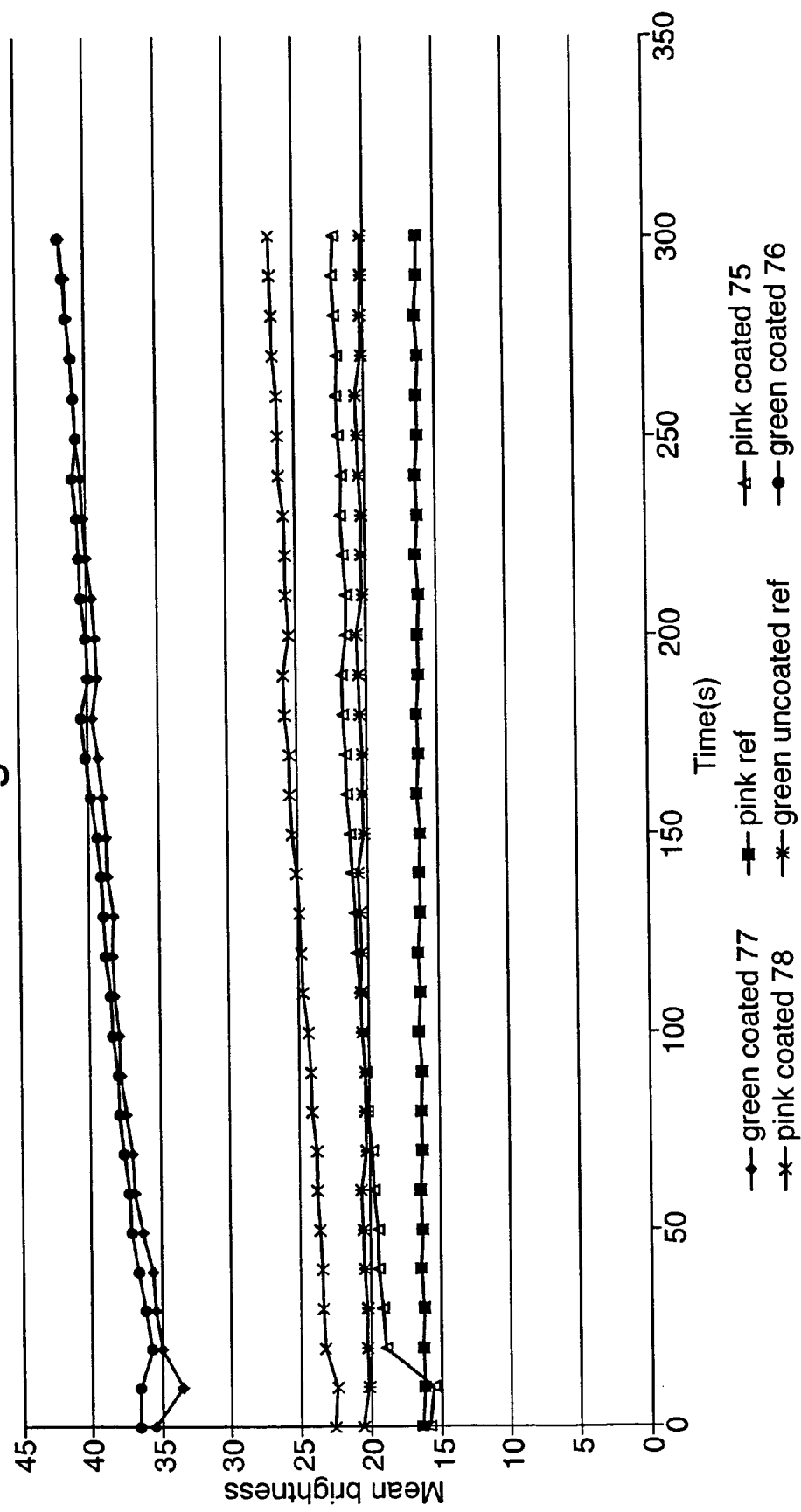

Upon analysis of the data, it was found that the most promising coatings on stainless steel plates (samples 63f–h) and those on needles (64 and 65 for trial set 1 and 75, 76, 77 and 78 for trial set 2), identified by eye and earlier video assessment, gave rise to the greatest quantitative changes, as shown in FIGS. 9–11. These were all coatings in which the layer order followed the scheme in which a layer of Hydrothane™ containing dissolved citric acid was deposited first and then overlaid with subsequent layers of Hydrothane™ only and Hydrothane™ containing sodium hydrogen carbonate. Samples where the order was reversed showed very little activity. The other more obvious factor, was that the most active coatings contained the most gas producing reagent i.e. >50%/wt assuming an equal ratio of the reactive components (0.25 g citric acid and 0.25 g sodium hydrogen carbonate in 1 g Hydrothane™).

3.2 Adhesion Tests

The test matrix with the average peel loads is defined in Table 1.

TABLE 1

Details of surface pretreatments and the results of the 180° Peel Test.
(key for needles used in FIG. 9)

| Surface Pretreatment | Sample Number | Average Peel Load Dry (N) | Sample Number. | Average Peel Load Wet (N) |
|---|---|---|---|---|
| Solvent degrease | 31–35 | 1.2 | 36–40 | 0.8 |
| Wet-Blast (W-B) | 41–45 | 6.0 | 46–50 | 4.0 |
| W-B + Chronoflex ™ | 51–55 | 5.0 | 56–60 | 2.0 |
| W-B + Acid Etch | 61–65 | 5.0 | 66–70 | 3.8 |
| W-B + Primer | 71–75 | 32.0 | 76–80 | 25.0 |

Note.
The force of 1 N is equivalent to applying a load of 0.1 kg

The data for each surface pretreatment (wet and dry) is provided above. The lowest bond strengths were found with specimens which were only degreased in acetone. Wet blasting increased the adhesion of coating by about a factor of five. Exposure to water degrades this adhesion by approximately 30%. The effects of the $FeCl_2$/HCl etch or the precoat of Chronoflex™ AL80A (a similar polyurethane to Hydrothane™) is shown to perform less well in the dry than wet blasting alone and the latter shows a further degradation in performance upon exposure to water.

The best results are obtained by using the chromate free water based primer from Cytec, where dry peel loads averaged 32N and wet ones were around 25N, over five times better than the wet blasted steel surface and over 25 times better than no treatment other than degreasing. It must be stressed that this primer is experimental in type and as such has no medical authority approval at this time, but it also must be remembered that the excellent adhesion afforded by this system would render contact of this primer to biological tissue negligible. However, should this primer be unsuitable, two options exist:
1. The primer is replaced by another system which has the appropriate approval.
2. The adhesion achieved by wet blasting only, is sufficient for the procedure, in which case the need for a primer may be eliminated.

3.3 Concentration of Gas Producing Reagents

Five concentrations of gas producing reagent were selected to be assessed—20, 50, 100, 150 and 200% by weight relative to the dry weight of Hydrothane™ i.e. for a 20%/wt solution of the polymer (0.1774 g/ml) the concentrations would be 0.0355, 0.089, 0.1774, 0.266 and 0.355 g/ml of a 50/50 mixture of citric acid to sodium hydrogen carbonate. Samples were prepared on both glass slides and stainless steel plates. Samples with a layer structure consisting of St|PU|PUC|PU|PUS were produced, where St represents the steel substrate, PU pure Hydrothane™, PUC Hydrothane™+citric acid and PUS Hydrothane™ +sodium hydrogen carbonate. Such a structure was selected on the basis of the quantitative evaluation detailed in 5.1.

Full details of the samples produced for video analysis and their qualitative assessment from the video data are provided in Table 2.

TABLE 2

Details of samples produced to investigate the effect of gas producing agent concentration and video qualitative assessment

| Specimen Number | Agent concentration %/wt for dry Hydrothane ™ | Speed of Initial Bubble Production | Distribution of Bubbles | Overall Rate of Bubble Production |
|---|---|---|---|---|
| 96 | 20 | 0 | 0 | 0 |
| 97 |  | 0 | 0 | 0 |
| 98 |  | 0 | 0 | 0 |
| 99 | 50 | 0 | 0 | 0 |
| 100 |  | 1 | 1 | 1 |
| 101 |  | 0 | 0 | 0 |
| 102 | 100 | 1 | 2 | 2 |
| 103 |  | 1 | 3 | 2 |
| 104 |  | 2 | 3 | 3 |
| 105 | 150 | 1 | 2 | 3 |
| 106 |  | 1 | 2 | 3 |
| 107 |  | 2 | 3 | 3 |
| 108 | 200 | 3 | 3 | 3 |
| 109 |  | 3 | 3 | 3 |
| 110 |  | 3 | 3 | 3 |

(0—no activity, 3—maximum activity).

Figure 12:
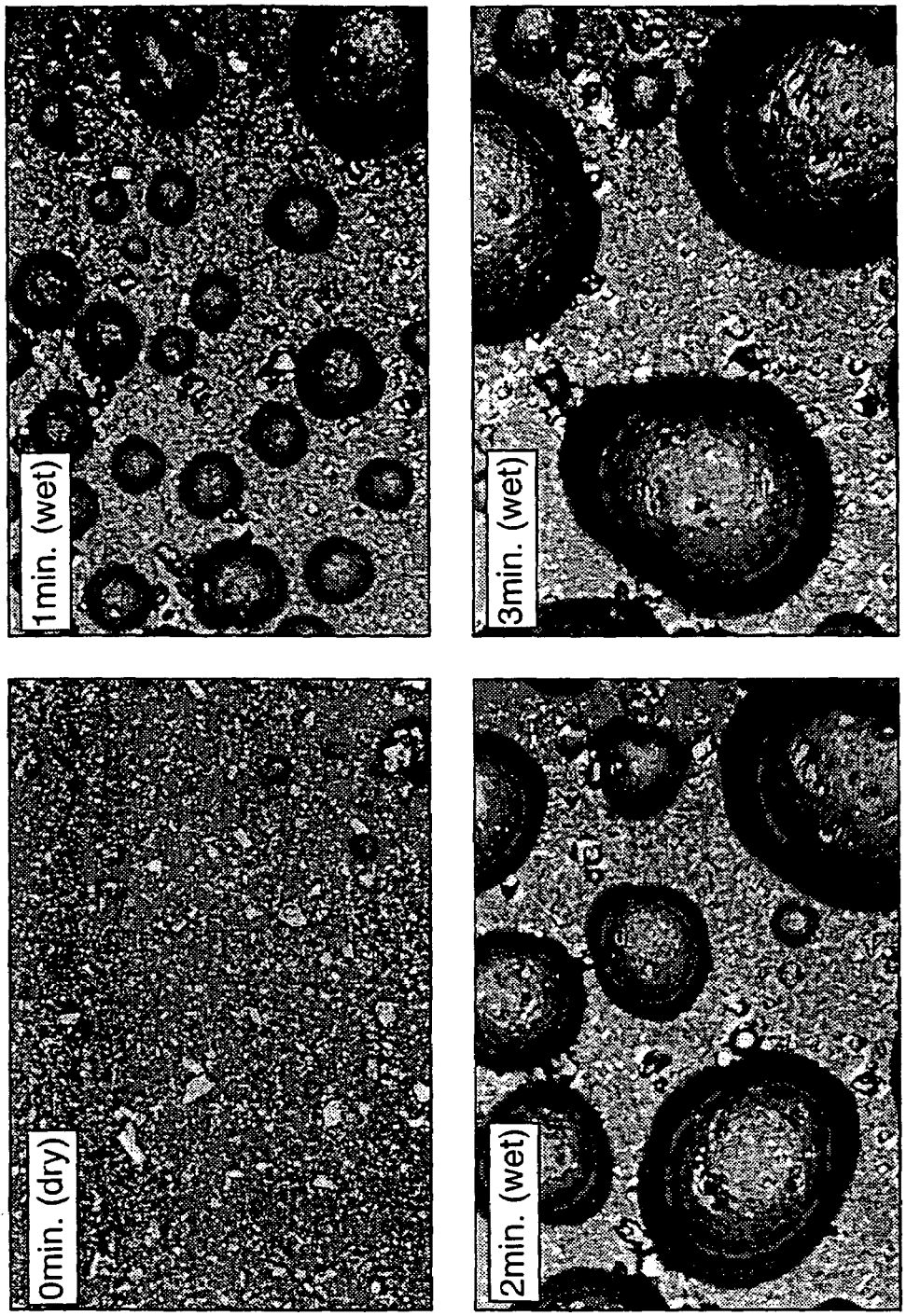
FIG. 12 is a artists representation of the bubble production from a coating cast on a glass slide "Sample No. 88"
Figure 14A:
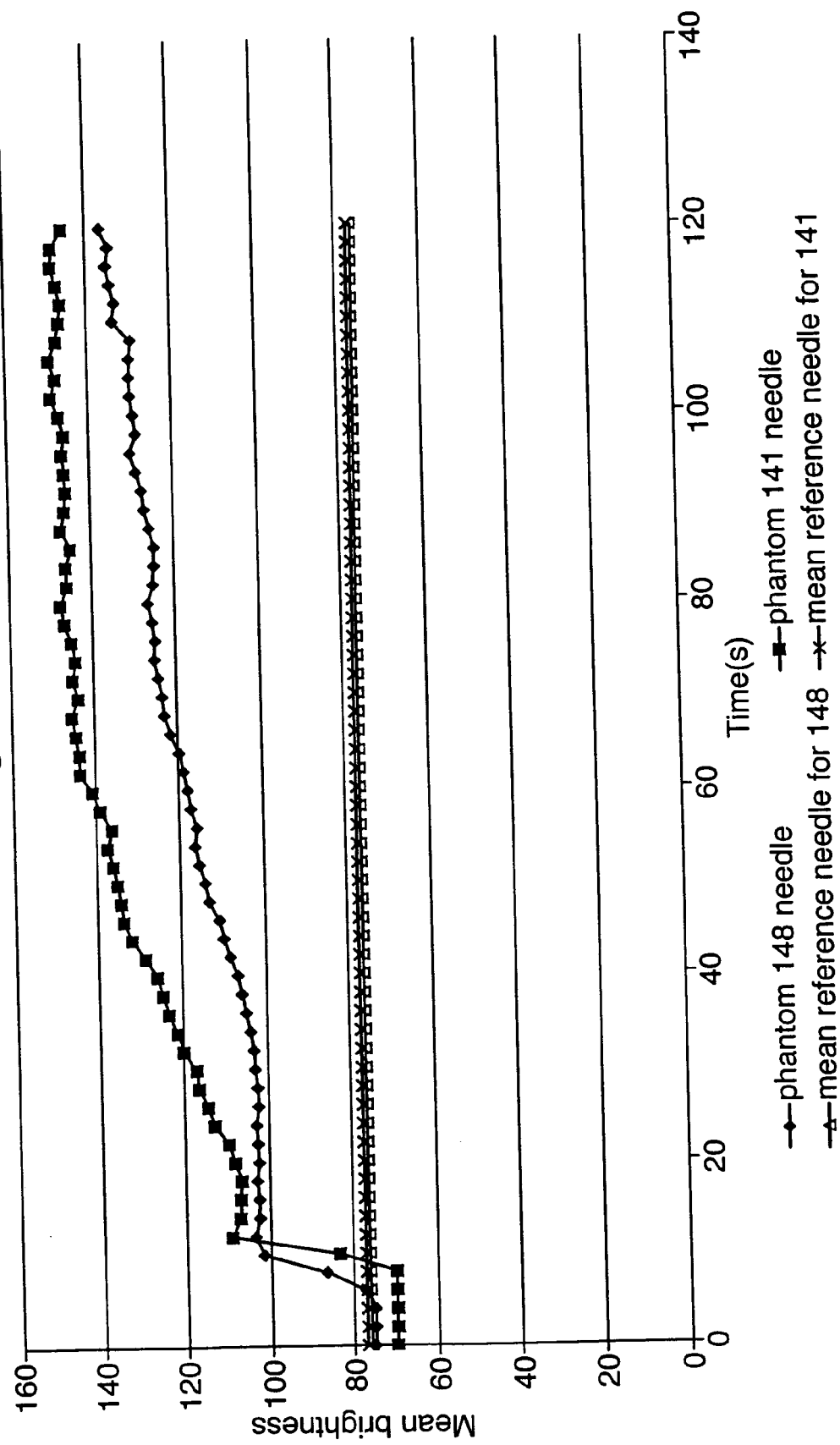
FIGS. 14A–14D show a quantitative analysis of ultrasound data for coating needles in a Tissue-Mimicking Phantom.
Figure 14B:
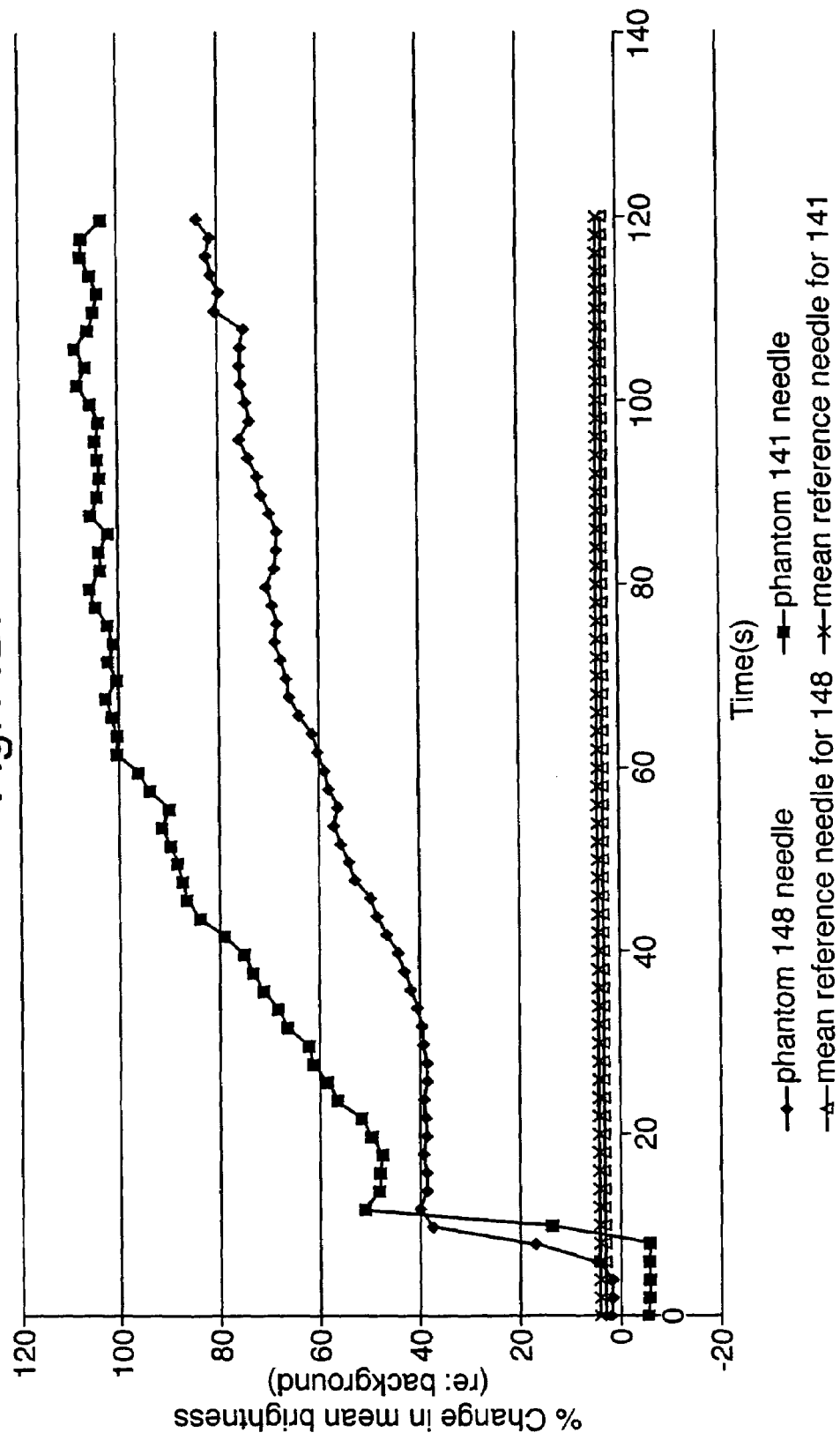
Figure 14C:
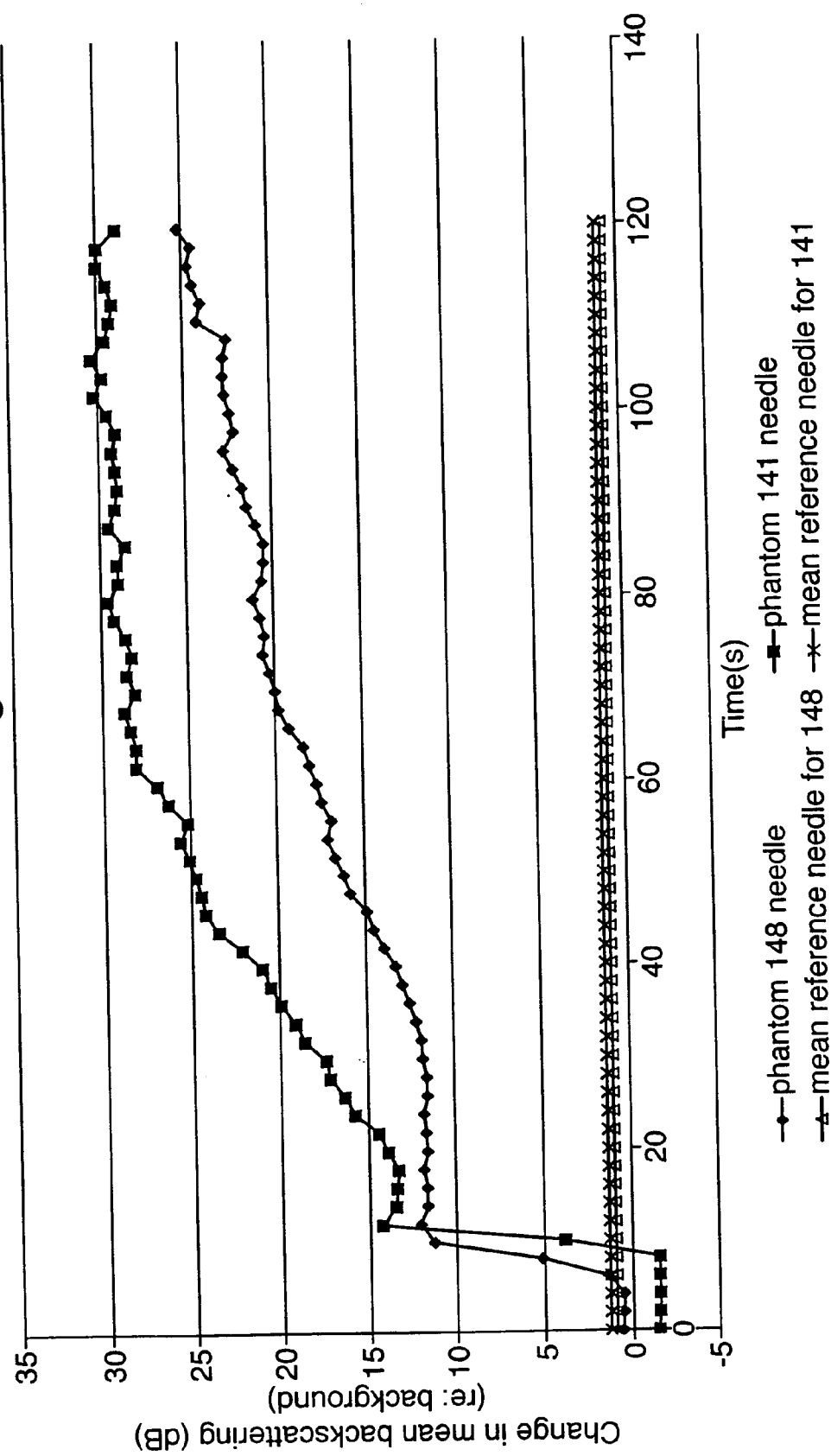
Figure 14D:
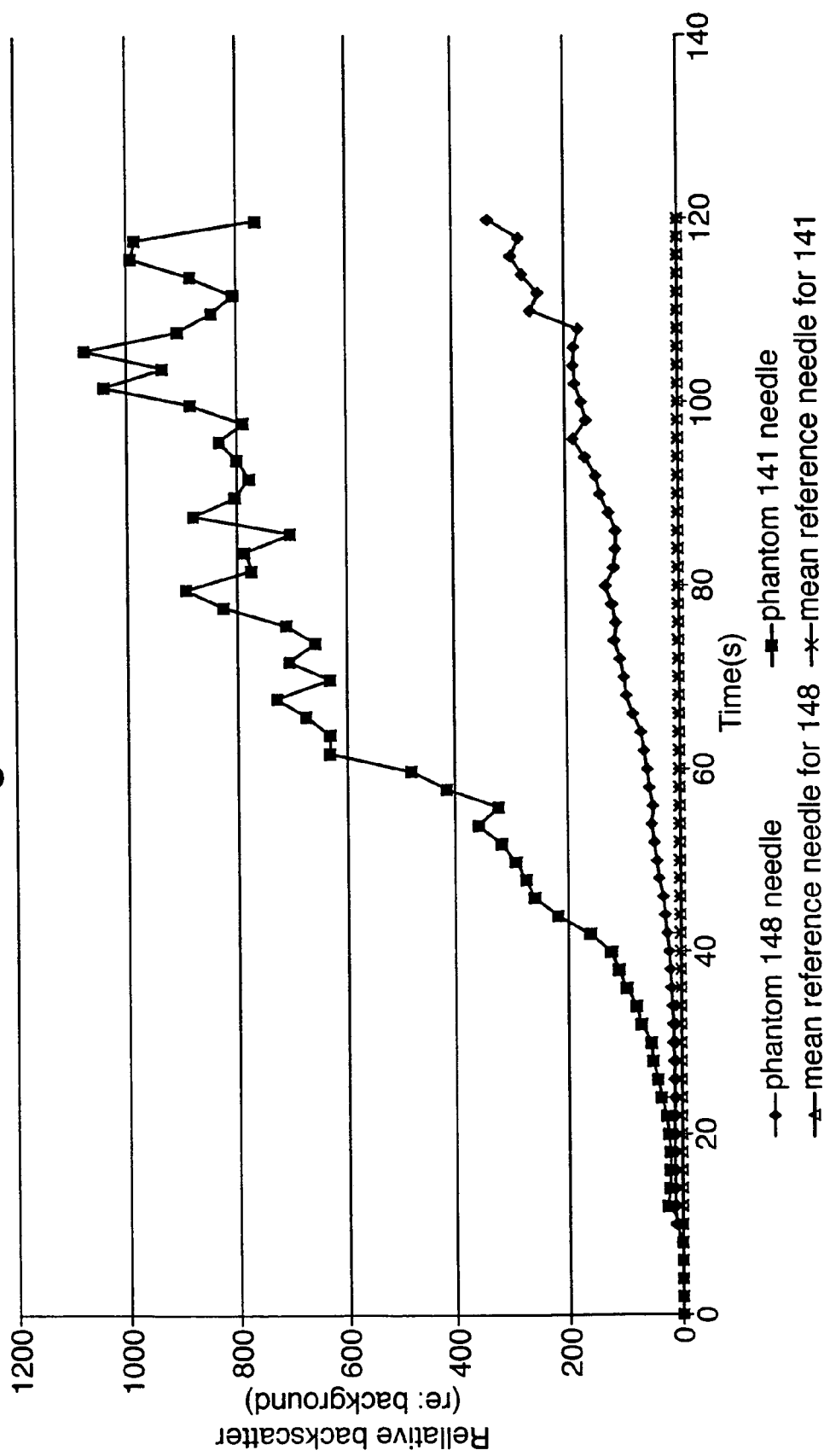

Evaluation was done using optical microscopy for coatings on glass slides and video microscopy for coatings on flat stainless steel plates. For the former, various photographs were taken at different times after exposure to water whereas for the latter, the video was converted into digital format and saved on a CDROM. Drawn copies of Images taken from the first techniques are shown in FIG. 12.

The primary trend was as expected, i.e. the rate of bubble production increased and became more rapid as the concentration of the reagents was increased. By digitising the data it was possible to obtain information relating to the time at which bubbles could first be observed. These times can then be plotted against the reagent concentration and it can be shown that an inverse power law can describe the data, FIG. 11. It is accepted that there is some considerable scatter in the data from the samples with the lowest concentrations of bubbling agent, thereby making the prediction unsafe for such levels. However, previous experience has shown that all coatings produced using lower levels of reagent are considerably slower in bubble production and it is felt that though further work would achieve a more accurate model, the trends observed would be the same. The power law indicates that a limit of around 5–10 seconds is the minimum time within which visible bubbles can be generated in the coating for a maximum amount of gas producing reagent.

3.4. Distribution of Gas Producing Reagents 3.4.1. Experiments Using Glass Slides and Stainless Steel Plates Coatings produced with four different layer structures were evaluated, using the optimum concentration of gas producing reagents, as derived from the work carried out in 5.3, i.e. 200% by weight (0.355 g/ml of a 50/50 mixture of citric acid to sodium hydrogen carbonate for a 20%/wt solution of the polymer, 0.1774 g/ml). A table describing the layer structures is given in Table 3. Evaluation was carried using microscopy for coatings on glass slides and video microscopy for coatings on flat stainless steel plates. To confirm further the importance of order of the reagent layers, one coating was prepared in which the citric acid layer was the last to be applied.

TABLE 3

Details of Coating Structures Applied to Plates/Slides for Microscopic Assessment

| Coating Number | Coating Structure |
|---|---|
| 1 | St|PUC|PU|PUS |
| 2 | St|PU|PUC|PU|PUS |
| 3 | St|PU|PUC|PUS |
| 4 | St|PU|PUS|PU|PUC |

Where:
St—Stainless steel substrate (or glass)
PU—Hydrothane ™
PUC—Hydrothane ™ + dissolved citric acid
PUS—Hydrothane ™ + sodium hydrogen carbonate particles A total of 24 coated samples were produced, to investigate the effect of the above layer structures. Full details are provided in Table 4.

TABLE 4

Samples produced to investigate the effect of the layer structure coating reactivity

| Substrate/Technique | Coating Number | | | |
|---|---|---|---|---|
|  | Coating 1 Sample | Coating 2 Sample | Coating 3 Sample | Coating 4 Sample |
| Glass slide/Microscope | 111 | 114 | 117 | 120 |
|  | 112 | 115 | 118 | 121 |
|  | 113 | 116 | 119 | 122 |
| Steel Plate/Video | 123 | 126 | 129 | 132 |
|  | 124 | 127 | 130 | 133 |
|  | 125 | 128 | 131 | 134 |

Analysis of the four coatings by both optical microscopy and video microscopy confirmed that if the citric acid layer is applied over the top of the layer containing sodium bicarbonate then the reactivity of the coating is severely impaired. For example, coatings 1, 2 and 3 gave rise to bubbles between 8 and 20 seconds whereas coating 4 tool over 6 minutes to produce similar levels of bubbles. This delay may be used to advantage in certain situations.

Little difference was seen between coatings 1 and 2 in terms of rate of bubble generation and bubble distribution, both could be produced with an even surface and with a minimum number of bubbles trapped within the matrix. Coating 3 had similar bubble producing activity to the first two, however it was extremely difficult to produce samples with few or no internal bubbles. It is assumed that these bubbles are the product of premature reaction between the reagents prior to complete solvent evaporation due a lack of a polyurethane dividing layer.

3.4.2. Experiments Using Biopsy Needles

To verify further the layer structure on the activity of the coatings, the two most promising coatings were selected (Coatings 1 and 2) to assess their behaviour on biopsy needles. Six coated biopsy needles were produced, three with each coating and evaluated using video microscopy and subsequently saved to CDROM. The details of these samples are provided in Table 5.

TABLE 5

Samples produced to investigate the effect of the layer structure coating reactivity on biopsy needles.

| Substrate/Technique | Coating Number | |
|---|---|---|
| | Coating 1 Sample | Coating 2 Sample |
| Needle/Video | 135 | 138 |
| | 136 | 139 |
| | 137 | 140 |

Analysis of the video data for this set of coated biopsy needles verified what had already been seen for the coated plates i.e. both coating structures gave rise to rapid, even bubble production over a period of four minutes or greater. The presence of a base layer of Hydrothane™ had no observable effect. The reduced area and curved shape of the needle surface did not appear to significantly affect the size or the rate of bubble evolution, unlike the previous observations in which where lower concentrations of reagent had been used.

It was also observed that the coating surfaces were relatively smooth and even over the needle surface. Evidence of voids/cavities within the coating could be seen for some samples but these were low in number and did not appear to affect the performance of the needles.

3.5. Production of Coated Biopsy Needles

On the basis of the work described above, it was decided to coat biopsy needles for trials using the coating of structure St|BP|PU|PUC|PU|PUS. Where BP designates wet blasting the surface followed by the water based Cytec primer. The reasoning for this coating structure is as follows:

Wet blasting followed by the water based primer was shown to improve the adhesion of the coating to stainless steel significantly. It is accepted that the adhesion strength of the primer to a smooth stainless steel surface has not been determined and it may well be sufficiently good to allow for the elimination of the wet blasting process. Further work to address this issue would be required.

A base layer of pure Hydrothane™ was incorporated because it was against this that the adhesion tests were made and the effect of a citric acid loaded polymer on the primed surface is not known. It is thought that such a layer should adhere sufficiently well, in which case the presence of a pure Hydrothane™ base layer is not absolutely necessary.

The next three layers of PUC|PU|PUS, in that order, have consistently been shown to give the most effective bubble producing properties. The need for a separating polyurethane layer may not be necessary if the premature reaction between the reagents in the two other layers could be suppressed, but this was not possible within the laboratory environment.

The addition of a top coating of Hydrothane™ was deemed to be unnecessary, in that it slowed down the initial rate of bubble production. Release of bubbles to the surface of the coating is not perceived to be a problem by members of the medical profession invited to assess the invention under conditions of confidentiality.

Using appropriate conditions and concentrations for the coating, as defined from this programme of work, a total of 29 biopsy needles were prepared, complete details of which are given in Table 6.

The concentration of reagent within the coating was 200%/wt of total reagent in the dry Hydrothane™ matrix i.e. 2 g citric acid in 1 g matrix and 2 g sodium hydrogen carbonate in 1 g matrix. The nominal pure Hydrothane™ solution concentration used was 20%/wt in THF or 0.1774 g/ml.

The production of the needles entailed an initial degrease operation, followed by light wet blasting (described in 5.2). Next the Cytec BR6757 primer was applied by dipping the needles into the solution. The needles were dipped but not sprayed, as in the previous work carried out on flat stainless steel, because the shape and size of the needles readily allowed the primer to dry. The needles were then cured in an oven at 100° C. for one hour. This was preferred at 100° C. instead of 120° C., as recommended, because of the possible degradation of the plastic ends of the needles. The needles were then coated with each layer of the Hydrothane™ by dipping them into the appropriate solution and suspending them vertically in air, at room temperature in a static fume cupboard until all of the solvent had evaporated. The dipping process was then repeated until all the layers had been applied. The coated needles were stored in a dessicator until required.

As for the previous set of coated needles, the coatings appeared smooth and even, with minimal numbers of internal voids/bubbles.

TABLE 6

Details of coated biopsy needles

| Needle Number | Needle colour | Pretreatment | Coating Structure |
|---|---|---|---|
| 141 | Pink | W-B, Primer | St|BP|PU|PUC|PU|PUS |
| 142 | Green | W-B, Primer | St|BP|PU|PUC|PU|PUS |
| 143 | Pink | W-B, Primer | St|BP|PU|PUC|PU|PUS |
| 144 | Pink | W-B, Primer | St|BP|PU|PUC|PU|PUS |
| 145 | Green | W-B, Primer | St|BP|PU|PUC|PU|PUS |
| 146 | Pink | W-B, Primer | St|BP|PU|PUC|PU|PUS |
| 147 | Pink | W-B, Primer | St|BP|PU|PUC|PU|PUS |
| 148 | Green | W-B, Primer | St|BP|PU|PUC|PU|PUS |
| 149 | Green | W-B, Primer | St|BP|PU|PUC|PU|PUS |
| 150 | Green | W-B, Primer | St|BP|PU|PUC|PU|PUS |
| 151 | Green | W-B, Primer | St|BP|PU|PUC|PU|PUS |
| 152 | Green | W-B, Primer | St|BP|PU|PUC|PU|PUS |
| 153 | Green | W-B, Primer | St|BP|PU|PUC|PU|PUS |
| 154 | Green | W-B, Primer | St|BP|PU|PUC|PU|PUS |
| 155 | Pink | W-B, Primer | St|BP|PU|PUC|PU|PUS |
| 156 | Pink | W-B, Primer | St|BP|PU|PUC|PU|PUS |
| 157 | Green | W-B, Primer | St|BP|PU|PUC|PU|PUS |
| 158 | Green | W-B, Primer | St|BP|PU|PUC|PU|PUS |
| 159 | Green | W-B, Primer | St|BP|PU|PUC|PU|PUS |
| 160 | Pink | W-B, Primer | St|BP|PU|PUC|PU|PUS |
| 161 | Pink | W-B, Primer | St|BP|PU|PUC|PU|PUS |
| 162 | Green | W-B, Primer | St|BP|PU|PUC|PU|PUS |
| 163 | Pink | W-B, Primer | St|BP|PU|PUC|PU|PUS |
| 164 | Green | W-B, Primer | St|BP|PU|PUC|PU|PUS |
| 165 | Green | W-B, Primer | St|BP|PU|PUC|PU|PUS |
| 166 | Pink | Primer | None |
| 167 | Green | Primer | None |
| 168 | Pink | Primer | St|PU|PUC|PU|PUS |
| 169 | Green | Primer | St|PU|PUC|PU|PUS |

3.6 Ultrasound Evaluation of Coated Biopsy Needles

One each of the green and pink needles prepared according to Table 6 and designated "Third Needle Series", was evaluated under ultrasound (see 3.2.3.4 above) in a tissue-mimicking phantom and in an isolated ovine liver. Uncoated needles of each diameter served as controls. The phantom consisted of tissue mimicking material (TMM) with acoustic properties similar to those of soft tissue. [1].

3.6.1. Tissue Mimicking Material (TMM)

The TMM was submerged in a water bath at 37° C. and the selected biopsy needles inserted into it. The ultrasound probe was held in place above the phantom, with the transducer elements submerged in the water. It should be noted that the spatial relationship between the probe and the needle was designed to replicate optimal conditions for image generation, rather than the "worst case", used in the earlier analysis. Images were acquired from the region of interest (ROI), digitised and stored, as described above, for further analysis. The data acquisition process was calibrated so that the relationship between the brightness of the digitised image and the actual reflectivity/backscatter (dB) was expressed by the following formula:

$$\text{Gain in } dB = 0.4 \times \text{brightness in } ROI + C \text{ (Where } C \text{ is a constant)}$$

Both the green and pink coated needles were readily visible in the resulting ultrasound image, when tested in the tissue mimicking phantom. Enhancement of the needles persisted throughout the imaging experiment, i.e. for greater than 100 seconds. The larger bore needle (pink) was more readily seen than the smaller needle (green). The attached graphs (FIGS. 14-A to 14-D) quantify the increased enhancement of the needles, compared with the uncoated controls. In particular, FIG. 14-C shows a peak mean backscatter of 25–30 dB, relative to the controls. The coated needles were visible within a few seconds of insertion and the rate of bubble generation, hence reflectivity, continued to increase, reaching a plateau after approximately 60 seconds.

3.6.2. Isolated Ovine Liver

The above experiments were repeated using an isolated ovine liver to evaluate the performance of the coated needles and commercial needles with echogenic tips, in solid tissue. The liver was obtained at the abattoir from a recently-slaughtered sheep, placed in a solution of heparinised normal saline and transported to St George's Hospital. The liver was placed in fresh heparinised saline under a gentle vacuum, to reduce the number of gaseous inclusions trapped inside the liver. Coated needles of both gauges were inserted into the isolated liver, as described above for the TMM. As before, the commercial uncoated needles of both gauges served as controls. For a further comparison, one of the coated needles was stripped of its coating at the end of the experiment to see if the roughening process used to promote adhesion of the coating did, itself, contribute to the brightness of the needle being imaged.

The coated needles were clearly seen in the images obtained in the isolated ovine liver. It was noted that a track of bubbles was still visible in the liver, once the needles had been removed. Consequently, the clinician is able to track a bright line during needle placement, which provides information about both the angle and position of the needle, relative to the target, rather than the single bright spot afforded by the tip of the echogenic needle. Furthermore, when the coating was completely stripped from one of the needles (pink), no background reflectivity due to roughening the needle surface to promote coating attachment, was seen.

From the above it will be appreciated that incorporation of a gas producing reagent mixture within a hydrophilic polyurethane matrix and applying this as a coating to an instrument such as a biopsy needle, significantly enhances the instrument's visibility under ultrasound over conventional systems. Additionally, the in-vitro experiment, using a TMM shows the coated needles are readily visible in the resulting ultrasound image, with a peak mean backscatter of 25–30 dB relative to uncoated control needles. Also, enhancement of the needles persisted throughout the imaging experiment (>100 seconds). Further, these improvements have been confirmed in an isolated ovine liver and therefore demonstrate the present invention is a practical solution to this problem.

The experiments directed to a method of manufacturing illustrate that the adhesion of the coating to, for example, the stainless steel surface can be improved by a factor of 5 by wet blasting the surface prior to application and by a factor of 25 by using an epoxy based priming system. It is probable that a more than satisfactory adhesion may be achieved by using this primer even without prior surface treatment of the needle.

In addition to the above, it is worth noting that increasing the concentration of gas producing reagents within the matrix has been shown to significantly increase the bubble production rate and activity up to a maximum of 200%/wt reagent to matrix. Whilst any further increase in reagents is predicted to have little significant effect, it will be appreciated that a greater proportion may be used as and when that is desirable.

Possibly the most important feature is the separation of the two gas producing reagents into two layers, possibly further separated by a layer of pure matrix, which has been shown to be extremely desirable for successful production of a coating which exhibits minimal pre-reaction of the reagents. Total removal of the middle layer may be feasible under the right production conditions.

The order in which the layers form the coating, has been shown to have a substantial effect on the performance of the coating, in terms of rate and level of bubble production. The layer containing citric acid is most preferably below that containing sodium hydrogen carbonate.

The experiments demonstrate that biopsy needles and the like can be coated easily through a simple dipping technique which produces samples with smooth coating of even thickness. Other production methods such as, for example, spraying may be used as and where appropriate.

REFERENCES

[1] Tierlink C J P M, Bezemer R A, et al. "Development of an Example Flow Test Object and Comparison of Five of these Test Objects, Constructed in Various Laboratories", Ultrasonics 1998 36 653–660

The invention claimed is:

1. An instrument insertable into a medium and being capable of detection by sonic imaging equipment comprising:
   an elongate member for insertion into said medium and having a region the position of which it is desirable to monitor;
   bubble generating means for generating a plurality of discrete mobile bubbles at said region, whereby said bubbles are detectable by sonic imaging equipment;
   said bubble generating means comprising two elements which, upon contact with each other in the presence of a fluid, react with each other to produce gas bubbles, said elements comprising first and second radially displaced layers of said elements within a fluid permeable carrier material.

2. An instrument as claimed in claim 1 further including a fluid permeable intermediate layer between said two elements containing layers.

3. An instrument as claimed in claim 2 in which said intermediate layer comprises a hydrophilic material.

4. An instrument as claimed in claim 1 including a primer layer on said instrument upon which said fluid permeable carrier material is deposited.

5. An instrument as claimed in claim 4 in which said primer layer comprises an acid etched layer.

6. An instrument as claimed in claim 4 in which said primer layer comprises a chromate free water based primer (Cytec BR6752) or Chronoflex™ AL80A.

7. An instrument as claimed in claim 1 in which said carrier material comprises a hydrophilic material.

8. An instrument as claimed in claim 1 in which said two elements comprise citric acid and sodium hydrogen carbonate.

9. An instrument as claimed in claim 8 in which the citric acid comprises dissolved citric acid.

10. An instrument as claimed in claim 1 in which said first layer comprises a radially inner layer and comprises citric acid and said second layer comprises a radially outer layer and comprises sodium hydrogen carbonate.

11. An instrument as claimed in claim 1 in which said first layer comprises a radially inner layer and comprises sodium hydrogen carbonate and said second layer comprises a radially outer layer and comprises citric acid.

12. An instrument as claimed in claim 1 in which said elongate member includes a prepared surface prepared by solvent degreasing or wet blasting.

13. An instrument as claimed in claim 12 when having a wet blasted surface.

14. An instrument as claimed in claim 1 in which the ratio of bubble generating means to carrier material in said first or said second layer is between 20% and 200% by weight.

15. An instrument as claimed in claim 1 in which the ratio of the two elements is substantially 50/50 (by weight).

16. An instrument as claimed in claim 1 in which said bubble generating means is provided at one or more discrete portions along said elongate member.

17. An instrument as claimed in claim 1 in which said bubble generating means is provided along a substantial length of said elongate member.

18. A method of producing an instrument as claimed in claim 1 comprising the steps of:
   c) depositing onto the instrument a first layer containing a first of two elements which, upon contact with each other in the presence of a liquid, react with each other to produce gas bubbles, and
   d) depositing onto the first layer a second layer containing a second of said two elements.

19. A method as claimed in claim 18 including the further step of depositing a fluid permeable intermediate layer between said first and second layers.

20. A method as claimed in claim 19 in which said intermediate layer comprises a hydrophilic material.

21. A method as claimed in claim 18 including the further step of depositing a primer layer onto said instrument prior to any of the layers as defined above.

22. A method as claimed in claim 21 in which said primer layer comprises an acid etched layer.

23. A method as claimed in claim 21 in which said primer layer comprises a chromate free water based primer (Cytec BR6752) or Chronoflex™ AL80A.

24. A method as claimed in claim 18 in which the first and second layers comprise a hydrophilic material.

25. A method as claimed in claim 18 in which said two elements comprise citric acid and sodium hydrogen carbonate.

26. A method as claimed in claim 25 in which said two elements comprise dissolved citric acid and sodium carbonate particles.

27. A method as claimed in claim 18 in which said first layer comprises citric acid and said second layer comprises sodium hydrogen carbonate.

28. A method as claimed in claim 18 in which said first layer comprises sodium hydrogen carbonate and said second layer comprises citric acid.

29. A method as claimed in claim 18 including the further step of preparing the instrument surface by solvent degreasing or wet blasting.

30. A method as claimed in claim 18 including the step of adding the first and second elements to a carrier material to form said layers and in which said elements are added to said carrier material in a ratio of between 20% and 200% by weight.

31. A method as claimed in claim 18 in which the two elements are added in a ratio of substantially 50/50 by weight.

32. A method as claimed in claim 18 including the step of applying the layers at one or more discrete portions along said elongate member.

* * * * *